US012810997B2

(12) United States Patent
Ozcan et al.

(10) Patent No.: US 12,810,997 B2
(45) Date of Patent: Nov. 24, 2026

(54) BIOPSY-FREE IN VIVO VIRTUAL HISTOLOGY OF TISSUE USING DEEP LEARNING

(71) Applicants: THE REGENTS OF THE UNIVERSITY OF CALIFORNIA, Oakland, CA (US); UNITED STATES GOVERNMENT AS REPRESENTED BY THE DEPARTMENT OF VETERANS AFFAIRS, Washington, DC (US)

(72) Inventors: Aydogan Ozcan, Los Angeles, CA (US); Jingxi Li, Los Angeles, CA (US); Yair Rivenson, Los Angeles, CA (US); Xiaoran Zhang, Los Angeles, CA (US); Philip O. Scumpia, Los Angeles, CA (US); Jason Garfinkel, Los Angeles, CA (US); Gennady Rubinstein, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 356 days.

(21) Appl. No.: 18/572,113

(22) PCT Filed: Jun. 29, 2022

(86) PCT No.: PCT/US2022/035609

§ 371 (c)(1),
(2) Date: Dec. 19, 2023

(87) PCT Pub. No.: WO2023/283091

PCT Pub. Date: Jan. 12, 2023

(65) Prior Publication Data

US 2024/0290473 A1 Aug. 29, 2024

Related U.S. Application Data

(60) Provisional application No. 63/219,785, filed on Jul. 8, 2021.

(51) Int. Cl.
*G16H 30/40* (2018.01)
*A61B 5/00* (2006.01)
(Continued)

(52) U.S. Cl.
CPC .......... *G16H 30/40* (2018.01); *A61B 5/0068* (2013.01); *A61B 5/0071* (2013.01);
(Continued)

(58) Field of Classification Search
CPC .... G16H 30/40; A61B 5/0068; A61B 5/0071; A61B 2503/42; A61B 5/4331;
(Continued)

(56) References Cited

U.S. PATENT DOCUMENTS 6,187,289 B1 * 2/2001 Richards-Kortum .......................... A61B 5/0071 424/9.1
7,843,572 B2 * 11/2010 Teamney .......... G01N 33/4833 356/479
(Continued)

FOREIGN PATENT DOCUMENTS

WO WO 2019/191697 10/2019
WO WO 2020/018154 1/2020
(Continued)

OTHER PUBLICATIONS

Combalia, Marc et al. "Digitally Stained Confocal Microscopy through Deep Learning." International Conference on Medical Imaging with Deep Learning (2018) (Year: 2018).*
(Continued)

*Primary Examiner* — Andrew M Moyer
(74) *Attorney, Agent, or Firm* — VISTA IP LAW GROUP LLP

(57) ABSTRACT

A deep learning-based system and method is provided that uses a convolutional neural network to rapidly transform in vivo reflectance confocal microscopy (RCM) images of
(Continued)

unstained skin into virtually-stained hematoxylin and eosin-like images with microscopic resolution, enabling visualization of epidermis, dermal-epidermal junction, and superficial dermis layers. The network is trained using ex vivo RCM images of excised unstained tissue and microscopic images of the same tissue labeled with acetic acid nuclear contrast staining as the ground truth. The trained neural network can be used to rapidly perform virtual histology of in vivo, label-free RCM images of normal skin structure, basal cell carcinoma and melanocytic nevi with pigmented melanocytes, demonstrating similar histological features of traditional histology from the same excised tissue. The system and method enables more rapid diagnosis of malignant skin neoplasms and reduces invasive skin biopsies.

27 Claims, 24 Drawing Sheets

(51) Int. Cl.
*G06T 7/00* (2017.01)
*G06T 15/08* (2011.01)

(52) U.S. Cl.
CPC ............ *G06T 7/0012* (2013.01); *G06T 15/08* (2013.01); *G06T 2207/20084* (2013.01); *G06T 2207/30088* (2013.01)

(58) Field of Classification Search
CPC ..... A61B 5/441; A61B 5/7267; G06T 7/0012; G06T 15/08; G06T 2207/20084; G06T 2207/30088; G06T 2207/10056; G06T 2207/20081; G06T 11/10; G06V 10/764; G06V 20/69; G06V 10/82; A61P 35/00
See application file for complete search history.

(56) References Cited

U.S. PATENT DOCUMENTS

| | | | |
|---|---|---|---|
| 11,222,415 B2 | 1/2022 | Ozcan et al. | |
| 11,262,286 B2 | 3/2022 | Ozcan et al. | |
| 11,501,544 B2 | 11/2022 | Ozcan et al. | |
| 11,514,325 B2 | 11/2022 | Ozcan et al. | |
| 11,995,810 B2 * | 5/2024 | Lau | G01N 1/30 |
| 12,249,063 B1 * | 3/2025 | Jackson | G06T 7/11 |
| 12,310,698 B2 * | 5/2025 | Zeng | A61B 5/0075 |
| 2011/0137178 A1 * | 6/2011 | Tearney | A61B 5/037 600/476 |
| 2017/0168285 A1 | 6/2017 | Ozcan et al. | |
| 2019/0294108 A1 | 9/2019 | Ozcan et al. | |
| 2019/0333199 A1 | 10/2019 | Ozcan et al. | |
| 2020/0340901 A1 | 10/2020 | Ozcan et al. | |
| 2020/0360538 A1 | 11/2020 | Kossatz et al. | |
| 2021/0043331 A1 | 2/2021 | Ozcan et al. | |
| 2021/0209337 A1 | 7/2021 | Ozcan et al. | |
| 2021/0264214 A1 | 8/2021 | Ozcan et al. | |
| 2021/0374381 A1 | 12/2021 | Ozcan et al. | |
| 2021/0382052 A1 | 12/2021 | Ozcan et al. | |
| 2022/0012850 A1 | 1/2022 | Ozcan et al. | |
| 2022/0058776 A1 | 2/2022 | Ozcan et al. | |
| 2022/0114711 A1 | 4/2022 | Ozcan et al. | |
| 2022/0122313 A1 | 4/2022 | Ozcan et al. | |
| 2022/0206434 A1 | 6/2022 | Ozcan et al. | |
| 2023/0030424 A1 | 2/2023 | Ozcan et al. | |
| 2023/0060037 A1 | 2/2023 | Ozcan et al. | |
| 2023/0085827 A1 | 3/2023 | Ozcan et al. | |

FOREIGN PATENT DOCUMENTS

| | | |
|---|---|---|
| WO | WO 2020/102546 | 5/2020 |
| WO | WO 2020/139835 | 7/2020 |
| WO | WO 2020/219468 | 10/2020 |
| WO | WO 2021/133847 | 7/2021 |
| WO | WO 2021/188839 | 9/2021 |
| WO | WO 2022/256206 | 12/2022 |
| WO | WO 2023/107844 | 6/2023 |

OTHER PUBLICATIONS

Gareau, Daniel S. “Feasibility of digitally stained multimodal confocal mosaics to simulate histopathology.” Journal of biomedical optics vol. 14,3 (2009): 034050. doi:10.1117/1.3149853 (Year: 2009).*

PCT International Preliminary Report on Patentability (Chapter I of the Patent Cooperation Treaty) for PCT/US2022/035609, Applicant: The Regents of the University of California, Form PCT/ISA/237, dated Jan. 18, 2024 (10 pages).

The extended European search report dated Oct. 4, 2024 for European Patent Application No. 22838254.5-1207, (7 pages).

Marc Combalia et al., Digitally Stained Confocal Microscopy through Deep Learning, Proceedings of Machine Learning Research, 102:121-129, (2019).

Jingxi Li et al., Biopsy-free in vivo virtual histology of skin using deep learning, Light: Science & Applications (2021) 10:233; https://doi.org/10.1038/s41377-021-00674-8.

Esther Abels et al., Computational pathology definitions, best practices, and recommendations for regulatory guidance: a white paper from the Digital Pathology Association, J Pathol (2019); 249: 286-294.

Mohamed Amgad et al., Report on computational assessment of Tumor Infiltrating Lymphocytes from the International Immuno-Oncology Biomarker Working Group, npj Breast Cancer (2020) 6:16 ; https://doi.org/10.1038/ s41523-020-0154-2 (13 pages).

Guha Balakrishnan et al., VoxelMorph: A Learning Framework for Deformable Medical Image Registration, arXiv:1809.05231v2 [cs.CV] Jan. 17, 2019 (16 pages).

Navid Borhani et al., Digital staining through the application of deep neural networks to multi-modal multi-photon microscopy, Biomedical Optics Express, vol. 10, No. 3 (Mar. 1, 2019), 1339-1350.

Marissa D’Alonzo et al., Semantic segmentation of reflectance confocal microscopy mosaics of pigmented lesions using weak labels, Scientific Reports, (2021), 11:3679, https://doi.org/10.1038/s41598-021-82969-9.

Kevin de Haan et al., Deep learning-based image reconstruction and enhancement in optical microscopy, IEEE, (2020) (18 pages).

Kevin de Haan et al., Deep learning-based transformation of H&E stained tissues into special stains, Nature Communications, (2021) 12:4884, https://doi.org/10.1038/s41467-021-25221-2, www.nature.com/naturecommunications (13 pages).

James A. Diao et al., Human-interpretable image features derived from densely mapped cancer pathology slides predict diverse molecular phenotypes, Nature Communications, (2021) 12:1613, https://doi.org/10.1038/s41467-021-21896-9 | www.nature.com/naturecommunications (15 pages).

Rebekah A. Drezek et al., Laser scanning confocal microscopy of cervical tissue before and after application of acetic acid, Am J Obstet Gynecol 2000;182:1135-9.

Babak Ehteshami Bejnordi et al., Diagnostic Assessment of Deep Learning Algorithms for Detection of Lymph NodeMetastases in Women With Breast Cancer, JAMA, (Dec. 12, 2017); 318(22): 2199-2210.

Andre Esteva et al., Dermatologist-level classification of skin cancer with deep neural networks, Nature. Feb. 2, 2017; 542(7639): 115-118. doi:10.1038/nature21056.

Michael G. Giacomelli et al., Virtual Hematoxylin and Eosin Transillumination Microscopy Using Epi-Fluorescence Imaging, (2016) PLoS ONE, 11(8): e0159337, doi:10.1371/journal.pone.0159337.

Ian J. Goodfellow et al., Generative Adversarial Nets, arXiv:1406.2661v1 [stat. ML] Jun. 10, 2014.

H. A. Haenssle et al., Man against machine: diagnostic performance of a deep learning convolutional neural network for dermoscopic

(56) References Cited

OTHER PUBLICATIONS melanoma recognition in comparison to 58 dermatologists, Annals of Oncology 29: 1836-1842 (2018), doi:10.1093/annonc/mdy166, Published online May 28, 2018.
Phillip Isola et al., Image-to-Image Translation with Conditional Adversarial Networks, arXiv:1611.07004v1 [cs.CV] Nov. 21, 2016.
Diederik P. Kingma et al., ADAM: a Method for Stochastic Optimization, arXiv:1412.6980v9 [cs.LG] Jan. 30, 2017.
Kivanc Kose et al., Segmentation of Cellular Patterns in Confocal Images of Melanocytic Lesions in vivo via a Multiscale Encoder-Decoder Network (MED-Net), Med Image Anal. (Jan. 2021) 67:101841, doi:10.1016/j.media.2020.101841.
Xudong Mao et al., Least Squares Generative Adversarial Networks, arXiv:1611.04076v3 [cs.CV] Apr. 5, 2017.
Takeru Miyato et al., Spectral Normalization for Generative Adversarial Networks, arXiv:1802.05957v1 [cs.LG] Feb. 16, 2018.
Ozan Oktay et al., Attention U-Net: Learning Where to Look for the Pancreas, arXiv:1804.03999v3 [cs.CV] May 20, 2018.
Yair Rivenson et al., Virtual histological staining of unlabelled tissue-autofluorescence images via deep learning, Nature Biomedical Engineering | www.nature.com/natbiomedeng, https://doi.org/10.1038/s41551-019-0362-y.
Yair Rivenson et al., Emerging Advances to Transform Histopathology Using Virtual Staining, BME Frontiers, vol. 2020, Article ID 9647163, 11 pages, https://doi.org/10.34133/2020/9647163.
Yair Rivenson et al., PhaseStain: the digital staining of label-free quantitative phase microscopy images using deep learning, Light: Science & Applications ( 2019) 8:23, https://doi.org/10.1038/s41377-019-0129-y.
Olaf Ronneberger et al., U-Net: Convolutional Networks for Biomedical Image Segmentation, arXiv:1505.04597v1 [cs.CV] May 18, 2015.
Amaro Taylor-Weiner et al., A Machine Learning Approach Enables Quantitative Measurement of Liver Histology and Disease Monitoring in NASH, Hepatology, vol. 74, No. 1, 2021.
Hongda Wang et al., Deep learning enables cross-modality super-resolution in fluorescence microscopy, Nat Methods. Jan. 2019; 16(1):103-110. doi:10.1038/s41592-018-0239-0.
Mchen Wu et al., Three-dimensional virtual refocusing of fluorescence microscopy images using deep learning, (2019) (47 pages).
Daniel Xia et al., Computationally-Guided Development of a Stromal Inflammation Histologic Biomarker in Lung Squamous Cell Carcinoma, Scientific Reports, (2018) 8:3941, DOI:10.1038/s41598-018-22254-4.
Yijie Zhang et al., Digital synthesis of histological stains using micro-structured and multiplexed virtual staining of label-free tissue, Light: Science & Applications ( 2020) 9:78, https://doi.org/10.1038/s41377-020-0315-y.
PCT International Search Report for PCT/US2022/035609, Applicant: The Regents of the University of California, Form PCT/ISA/210 and 220, dated Oct. 6, 2022 (3 pages).
PCT Written Opinion of the International Search Authority for PCT/US2022/035609, Applicant: The Regents of the University of California, Form PCT/ISA/237, dated Oct. 6, 2022 (8 pages).
Piergiacomo Calzavara-Pinton et al., Reflectance Confocal Microscopy for In Vivo Skin Imaging, Photochemistry and Photobiology, vol. 84, Issue 6, p. 1421-1430.
Dr Rebecca Pool, Virtual staining set to reduce need for skin biopsies, Nov. 19, 2021, [retrieved on Sep. 15, 2022], retrieved from the Internet:URL:https://analyticalscience.viley.com/do/10.1002/was.00020445> pp. 1-4.
Communication under Rule 71(3) EPC Intention to grant dated Apr. 17, 2026 for European Patent Appl No. 22838254.5 (9 pages).

* cited by examiner

Conventional H&E histology

BIOPSY-FREE IN VIVO VIRTUAL HISTOLOGY OF TISSUE USING DEEP LEARNING

RELATED APPLICATION

This Application is a U.S. National Stage filing under 35 U.S.C. § 371 of International Application No. PCT/US2022/035609, filed on Jun. 29, 2022, which claims priority to U.S. Provisional Patent Application No. 63/219,785 filed on Jul. 8, 2021, which is are hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with government support under Grant Number 1926371, awarded by the National Science Foundation. The government has certain rights in the invention. This work was supported by the U.S. Department of Veterans Affairs, and the federal government has certain rights in the invention.

TECHNICAL FIELD

The technical field generally relates to deep neural networks and their use to create biopsy-free virtually stained images using images obtained of living tissue. The system and method has particular application to reflectance confocal microscopy (RCM) but may be extended to other imaging modalities such as multiphoton microscopy (MPM) and others. More particularly, the technical field relates to systems and methods that utilize trained deep neural networks to rapidly transform in vivo optical biopsy images (e.g., RCM images) of unstained skin into virtually-stained images.

BACKGROUND

Microscopic evaluation of histologically processed and chemically stained tissue is the gold standard for the diagnosis of a wide variety of medical diseases. Advances in medical imaging techniques, including magnetic resonance imaging, computed tomography, and ultrasound, have transformed medical practice over the past several decades, decreasing the need for invasive biopsies and exploratory surgeries. Similar advances in imaging technologies to aid in the diagnosis of skin disease non-invasively have been slower to progress.

Skin cancers represent the most common type of cancer diagnosed in the world. Basal cell carcinoma (BCC) comprises 80% of the 5.4 million skin cancers seen in the United States annually. Melanoma represents a small percentage of overall skin cancers but represents the leading cause of death from skin cancer and is among the deadliest cancers when identified at advanced stages. Invasive biopsies to differentiate BCC from benign skin neoplasms and melanoma from benign melanocytic nevi represent a large percentage of the biopsies performed globally. Over 8.2 million skin biopsies are performed to diagnose over 2 million skin cancers annually in the Medicare population alone, resulting in countless unnecessary biopsies and scars at a high financial burden. In addition, the process of biopsy, histological tissue processing, delivery to pathologists, and diagnostic assessment requires one day to several weeks for a patient to receive a final diagnosis, resulting in lag time between the initial assessment and definitive treatment. Thus, non-invasive imaging presents an opportunity to prevent unnecessary skin biopsies while improving early detection of skin cancer.

The most used ancillary optical imaging tool used by dermatologists are dermatoscopes, which magnify skin lesions and use polarized light to assess superficial features of skin disease and triage lesions with ambiguous features for tissue biopsy. While dermatoscopes can reduce biopsies in dermatology, their use requires proper training to improve sensitivity of detecting skin cancers over clinical inspection alone. More advanced optical technologies have been developed for non-invasive imaging of skin cancers, including reflectance confocal microscopy (RCM), optical coherence tomography (OCT), multiphoton microscopy (MPM), and Raman spectroscopy, among others. Of these optical imaging technologies, only RCM and MPM technologies provide cellular-level resolution similar to tissue histology and allow for better correlation of image outputs to histology due to their ability to discern cellular-level details.

RCM imaging detects backscattered photons that produce a grayscale image of tissue based on contrast of relative variations in refractive indices and sizes of organelles and microstructures. Currently, RCM can be considered as the most clinically-validated optical imaging technology with strong evidence supporting its use by dermatologists to discriminate benign from malignant lesions with high sensitivity and specificity. Importantly, several obstacles remain for accurate interpretation of RCM images, which requires extensive training for novice readers. While the black and white contrast images can be used to distinguish types of cells and microstructural detail, in vivo RCM does not show nuclear features of skin cells in a similar fashion to traditional microscopic evaluation of tissue histology. Multimodal ex vivo fluorescence and RCM can produce digitally-colorized images with nuclear morphology using fluorescent contrast agents. However, these agents are not used n vivo with a reflectance-based confocal microscopy system. Without nuclear contrast agents, nuclear features critical for assessing cytologic atypia are not discernable. Further, the grayscale image outputs and horizontal imaging axis of confocal technologies pose additional challenges for diagnosticians who are accustomed to interpreting tissue pathology with nuclear morphology in the vertical plane. Combined, these visualization-based limitations, in comparison to standard-of-care biopsy and histopathology, pose barriers for wide adoption of RCM.

On the other hand, hematoxylin and eosin (H&E) staining of tissue sections on microscopy slides represents the most common visualization format used by dermatologists and pathologists to evaluate skin pathology. Thus, conversion of images obtained by non-invasive skin imaging and diagnostic devices to an H&E-like format may improve the ability to diagnose pathological skin conditions by providing a virtual "optical biopsy" with cellular resolution and in an easy-to-interpret visualization format.

Deep learning represents a promising approach for computationally-assisted diagnosis using images of skin. Deep neural networks trained to classify skin photographs and/or dermoscopy images, successfully discriminated benign from malignant neoplasms at similar accuracy to trained dermatologists. Algorithms based on deep neural networks can help pathologists identify important regions of disease, including microscopic tumor nodules, neoplasms, fibrosis, inflammation, and even allow prediction of molecular pathways and mutations based on histopathological features. Researchers also used deep neural networks to perform semantic segmentation of different textual patterns in RCM mosaic images of melanocytic skin lesions as a potential diagnostic aid for clinicians. Deep learning-based approaches have also enabled the development of algorithms to learn image transformations between different microscopy modalities to digitally enhance pathologic interpretation. For instance, using unstained, autofluorescence images of label-free tissue sections, a deep neural network can virtually stain images of the slides, digitally matching the brightfield microscopy images of the same samples stained with standard histochemical stains such as H&E, Jones, Masson's Trichrome and periodic acid Schiff (PAS) without the need for histochemical processing of tissue. These virtually-stained images were found to be statistically indiscernible to pathologists when compared in a blinded fashion to the images of the chemically stained slides. Deep learning-enabled virtual staining of unstained tissue has been successfully applied to other types of label-free microscopic imaging modalities including e.g., quantitative phase imaging and two photon excitation with fluorescence lifetime imaging, but has not been used to obtain in vivo virtual histology.

SUMMARY

In one embodiment, a deep learning-based virtual tissue staining system and method is disclosed that rapidly performs in vivo virtual histology of unstained skin. In the training phase of this framework, RCM images were used of excised skin tissue with and without acetic acid nuclear contrast staining to train a deep convolutional neural network (CNN) using structurally-conditioned generative adversarial networks (GAN), together with attention gate modules that process three-dimensional (3D) spatial structure of tissue using 3D convolutions. First, time-lapse RCM image stacks are acquired of ex vivo skin tissue specimens during the acetic acid staining process to label cell nuclei. Using this 3D data, label-free, unstained image stacks were accurately registered to the corresponding acetic acid-stained 3D image stacks, which provided a high degree of spatial supervision for the neural network to map 3D features in label-free RCM images to their histological counterparts. Once trained, this virtual staining framework was able to rapidly transform in vivo RCM images into virtually stained, 3D microscopic images of normal skin. BCC, and pigmented melanocytic nevi with H&E-like color contrast. When compared to traditional histochemically-processed and stained tissue sections, this digital technique demonstrates similar morphological features that are observed in H&E histology. In vivo virtual staining of unprocessed skin through non-invasive imaging technologies such as RCM would be transformative for rapid and accurate diagnosis of malignant skin neoplasms, also reducing unnecessary skin biopsies.

In another embodiment, a method of using in vivo reflectance confocal microscopy (RCM) images of unstained tissue to generate digitally histological-stained microscopic images of tissue. The method includes providing a first trained, deep neural network that is executed by image processing software, wherein the first trained deep neural network receives as input(s) a plurality of in vivo RCM images of tissue and outputs a digitally acetic acid-stained image that is substantially equivalent to an image of actual acetic acid-stained tissue; and providing a second trained, deep neural network that is executed by image processing software, wherein the second trained, deep neural network receives as input(s) a plurality of n vivo RCM images of tissue and/or the corresponding digitally acetic acid-stained images from the first trained, deep neural network and outputs digitally histological-stained images that are substantially equivalent to the images achieved by actual histological staining of tissue. A plurality of in vivo RCM images of the tissue are obtained and are input to the first trained, deep neural network to obtain digitally acetic acid-stained images of the tissue. The plurality of in vivo RCM images and/or and the corresponding digitally acetic acid-stained images are input to the second trained, deep neural network, wherein the second trained, deep neural network outputs the digitally histological-stained microscopic images of the tissue.

In another embodiment, a system is disclosed for generating digitally histological-stained microscopic images from in vivo reflectance confocal microscopy (RCM) images of unstained tissue. The system includes a computing device having image processing software executed thereon or thereby, the image processing software comprising (1) a first trained, deep neural network, wherein the first trained, deep neural network receives as input(s) a plurality of in vivo RCM images of unstained tissue and outputs digitally acetic acid-stained images that are substantially equivalent to the images of the actual acetic acid-stained tissue; and/or (2) a second trained, deep neural network, wherein the second trained, deep neural network receives as input(s) a plurality of in vivo RCM images of unstained tissue and/or the corresponding digitally acetic acid-stained images from the first trained, deep neural network and outputs digitally histological-stained images that are substantially equivalent to the images achieved by actual histological staining of tissue.

In another embodiment, a method of using in vivo images of unstained tissue to generate digitally histological-stained microscopic images of tissue is disclosed. The method includes providing a first trained, deep neural network that is executed by image processing software, wherein the first trained deep neural network receives as input(s) a plurality of in vivo images of unstained tissue and outputs a digitally acetic acid-stained image of the tissue that is substantially equivalent to the image of the actual acetic acid-stained tissue; and providing a second trained, deep neural network that is executed by image processing software, wherein the second trained, deep neural network receives as input(s) a plurality of in vivo images of tissue and/or the corresponding digitally acetic acid-stained images from the first trained, deep neural network and outputs digitally histological-stained images that are substantially equivalent to the images achieved by actual histological staining of tissue. A plurality of in vivo images of the tissue are obtained and input to the first trained, deep neural network to obtain digitally acetic acid-stained images of the tissue. The plurality of in vivo images and/or and the corresponding digitally acetic acid-stained images are inputted to the second trained, deep neural network, wherein the second trained, deep neural network outputs the digitally histological-stained microscopic images of the tissue.

BRIEF DESCRIPTION OF THE DRAWINGS

FIGS. 3A-3E are violin plots show quantitative comparisons of the statistical distribution of the measured nuclear morphological parameters between the acetic acid virtually stained skin tissue images (network output) and their corresponding ground truth images obtained using actual acetic acid staining (ground truth). Five metrics are used for the comparison: (a) nuclear size, (b) contrast, (c) eccentricity, (d) concentration, and (f) compactness (see Methods for details). The statistical results cover a total number of 96,731 nuclei, detected in 176 ex vivo tissue images of normal skin. FIGS. 3F and 3G are violin plots shows the statistical distribution of the PCC values (FIG. 3F) and SSIM values (FIG. 3G) measured through comparing the virtually stained (acetic acid) tissue images against their corresponding actual acetic acid-stained ground truth images. In all the violin plots presented above, the dashed lines from top to bottom represent the 75%, 50% (median) and 25% quartile, respectively

FIG. 7A shows an overview. FIG. 7B shows initial registration. FIG. 7C shows $1^{st}$ or $2^{nd}$ fine registration. FIG. 7D shows training of network B in the $2^{nd}$ fine registration.

FIG. 8A illustrates the generator network while FIG. 8B illustrates the discriminator. A plurality of RCM images are used to generate the digitally stained image(s).

FIG. 9A is a bright-field H&E image of a skin tissue section cut horizontally through dermal-epidermal junction. FIG. 9B is a bright-field H&E image of a skin tissue section cut vertically. Pigmented melanocytes that are stained dark brown can be clearly observed.

FIG. 16A illustrates Generator loss as a function of the number of iterations. FIG. 16B illustrates Discriminator loss as a function of the number of iterations.

FIG. 18A illustrates the generator network while FIG. 18B illustrates the discriminator network. RCM images of unstained tissue and acetic acid-stained tissue are used to generate the pseudo-H&E stained images. Note that the ground truth is analytically computed as described herein.

DETAILED DESCRIPTION OF ILLUSTRATED EMBODIMENTS

Figure 1A:
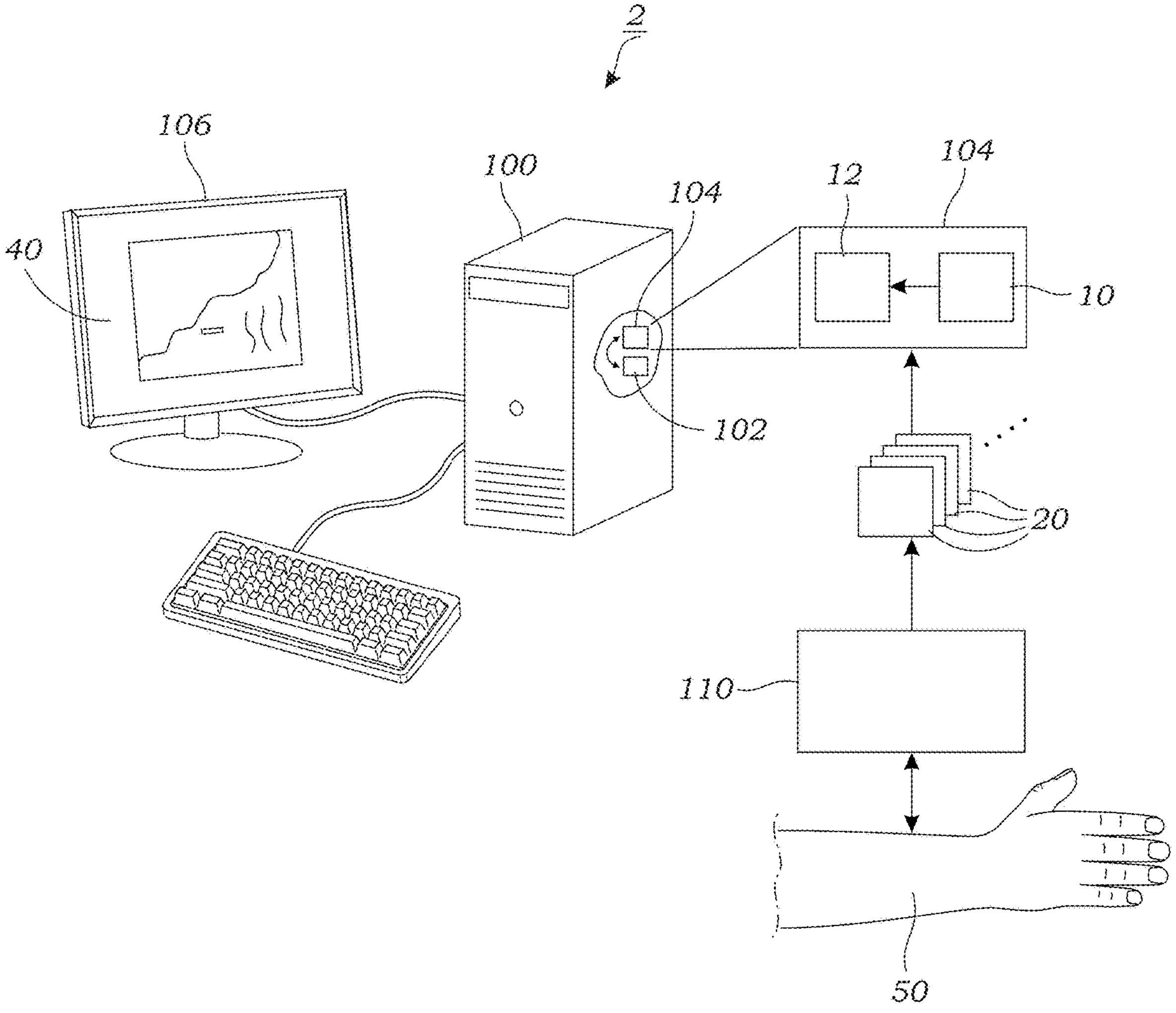
FIG. 1A schematically illustrates a system for generating or outputting digitally stained microscopic images from microscopy images of unstained tissue.

FIG. 1A schematically illustrates one embodiment of a system 2 for generating or outputting digitally stained microscopic images 40 from microscopy images 20 of unstained tissue 50. In one preferred embodiment, the microscopy images 20 are in vivo reflectance confocal microscopy (RCM). As explained herein, in one embodiment, the digitally stained microscopic images 40 of tissue 50 are substantially equivalent to images of the tissue 50 that were actually chemically stained with hematoxylin and eosin (H&E). While H&E stain is one stain that can be substantially digitally replicated, other chemical/histological stains may be similarly digitally replicated. This includes, for example, the following stains: Hematoxylin and Eosin (H&E) stain, hematoxylin, eosin. Jones silver stain, Masson's Trichrome stain, Periodic acid-Schiff (PAS) stains, Congo Red stain, Alcian Blue stain, Blue Iron, Silver nitrate, trichrome stains, Ziehl Neelsen, Grocott's Methenamine Silver (GMS) stains, Gram Stains, acidic stains, basic stains, Silver stains. Nissl, Weigert's stains, Golgi stain, Luxol fast blue stain, Toluidine Blue, Genta, Mallory's Trichrome stain, Gomori Trichrome, van Gieson, Giemsa, Sudan Black, Perls' Prussian, Best's Carmine. Acridine Orange, immunofluorescent stains, immunohistochemical stains, Kinyoun's-cold stain, Albert's staining, Flagellar staining, Endospore staining, Nigrosin, or India Ink stain.

As explained herein, the in vivo reflectance confocal microscopy (RCM) images 20 of tissue 50 are obtained from tissue 50 that is not stained or labeled. The tissue 50 may include skin tissue, cervical tissue, mucosal tissue, epithelial tissue, and the like. The in vivo reflectance confocal microscopy (RCM) images 20 (or other microscopy images 20) preferably comprise a plurality of such images 20 that are obtained from a microscope 110. For example, for RCM images 20, these are obtained with a RCM microscope 110 or other device for obtaining RCM images 20. For example, the plurality of images 20 may include an image stack of separate images focused at different depths within the tissue 50. The RCM microscope 110 may include different types of RCM microscopes 110 including stand-alone, bench-top, and portable devices.

In another embodiment, the system 2 is used to process images 20 of unstained tissue 50 obtained using a different type of microscope 110 used to obtained optical biopsy images of unstained tissue 50. This includes, for example, images 20 obtained from one or more of the following microscopes or imagers 110: a multiphoton microscope (MPM), a fluorescence confocal microscope/imager, a fluorescence microscope/imager, a fluorescence lifetime microscope (FLIM), a structured illumination microscope/imager, a hyperspectral microscope/imager, a Raman microscope/imager, and a polarization microscope/imager.

The system 2 includes a computing device 100 that contains one or more processors 102 therein and image processing software 104 that incorporates a first trained, deep neural network 10 (e.g., a convolutional neural network as explained herein in one or more embodiments) and a second trained, deep neural network 12 (e.g., a convolutional neural network as explained herein in one or more embodiments). As explained herein, the first deep neural network 10 is trained, in one embodiment, with matched acetic acid-stained images or image patches and their corresponding reflectance confocal microscopy (RCM) images or image patches of unstained ex vivo tissue samples, wherein the first trained deep neural network 10 outputs images 36 that are digitally stained that are substantially equivalent to images of the actual acetic acid-stained tissue (i.e., chemically stained). Of course, in embodiments that use a non-RCM microscope 110 (e.g., MPM, fluorescence confocal microscopy, structured illumination microscopy, and polarization microscopy), the corresponding images or image patches would be obtained with the same imaging modality for training.

These images 36 that are output from the first trained deep neural network 10 are thus virtually or digitally stained with acetic acid in response to the training. The second deep neural network 12 network is trained, in one embodiment, with matched ground truth pseudo-H&E images that were mathematically arrived at (or images of actual histologically stained tissue) and acetic acid-stained images or image patches and their corresponding reflectance confocal microscopy (RCM) images or image patches of unstained tissue samples (other stains may also be trained in a similar manner). Once trained, the first trained, deep neural network 10 receives a plurality of in vivo RCM images 20 of the unstained tissue 50 to obtain images 36 digitally stained with acetic acid. The second trained, deep neural network 12 receives a plurality of in vivo RCM images 20 and/or the corresponding digitally stained images 36 with acetic acid from the first trained, deep neural network 10, wherein the second trained, deep neural network 12 outputs digitally stained microscopic images 40 of the tissue 50 that are substantially equivalent to the images achieved by the actual histological staining of tissue (e.g., H&E in one embodiment). In some embodiments, the second trained, deep neural network 12 receives just the corresponding digitally stained images 36 output from the first trained, deep neural network 10 and uses these to output digitally stained images 40 that are substantially equivalent to the images achieved by the actual histologically stained tissue (e.g., H&E stain). The digitally stained microscopic images 40 may include a specific region of interest (ROI) of the tissue 40. The images 40 may also form a larger area or mosaic that is formed through digital stitching of images using image processing software 104. The images 40 may also be used to create a three-dimensional image or volume. Likewise, the images 40 may be used to show a particular plane (e.g., horizontal or vertical plane of the tissue 50).

The computing device 100 may include, as explained herein, a personal computer, laptop, mobile computing device, remote server, or the like, although other computing devices may be used (e.g., devices that incorporate one or more graphic processing units (GPUs) or other application specific integrated circuits (ASICs)). GPUs or ASICs can be used to accelerate training as well as final image output. The computing device 100 may be associated with or connected to a monitor or display 106 that is used to display the digitally stained microscopic images 40. The display 106 may also be used to display the grayscale RCM images. The user may be able to see both simultaneously or toggle between views. The display 106 may be used to display a Graphical User Interface (GUI) that is used by the user to display and view the digitally stained microscopic images 40 (or RCM or other microscopy images 20). In one embodiment, the user may be able to trigger or toggle manually between digitally stained microscopic images 40 or grayscale RCM images 20 using, for example, the GUI. In one preferred embodiment, the trained, deep neural network 10 is a Convolution Neural Network (CNN). In some embodiments, real-time digitally stained microscopic images 40 are generated which may be displayed to the user on the display 106.

For example, in one preferred embodiment as is described herein, the trained, deep neural networks 10, 12 are trained using a GAN model. In a GAN-trained deep neural network 10, 12, two models are used for training. A generative model is used that captures data distribution while a second model estimates the probability that a sample came from the training data rather than from the generative model. Details regarding GAN may be found in Goodfellow et al., Generative Adversarial Nets., Advances in Neural Information Processing Systems, 27. pp. 2672-2680 (2014), which is incorporated by reference herein. Network training of the deep neural networks 10, 12 (e.g., GAN) may be performed the same or different computing device 10. For example, in one embodiment a personal computer may be used to train the networks 10, 12 although such training may take a considerable amount of time. To accelerate this training process, one or more dedicated GPUs may be used for training. As explained herein, such training and testing was performed on GPUs obtained from a commercially available graphics card. Once the deep neural networks 10, 12 have been trained, the deep neural networks 10, 12 may be used or executed on the same or a different computing device 100 which may include one with less computational resources used for the training process (although GPUs may also be integrated into execution of the trained deep neural networks 10, 12).

The image processing software 104 can be implemented using Python and TensorFlow although other software packages and platforms may be used. MATLAB may be used for image registration algorithms as explained herein. The trained deep neural networks 10, 12 are not limited to a particular software platform or programming language and the trained deep neural networks 10, 12 may be executed using any number of commercially available software languages or platforms. The image processing software 104 that incorporates or runs in coordination with the trained, deep neural networks 10, 12 may be run in a local environment or a remote cloud-type environment. In some embodiments, some functionality of the image processing software 104 may run in one particular language or platform (e.g., image registration) while the trained deep neural networks 10, 12 may run in another particular language or platform. Nonetheless, both operations are carried out by image processing software 104.

EXPERIMENTAL

Results

Figure 1B:
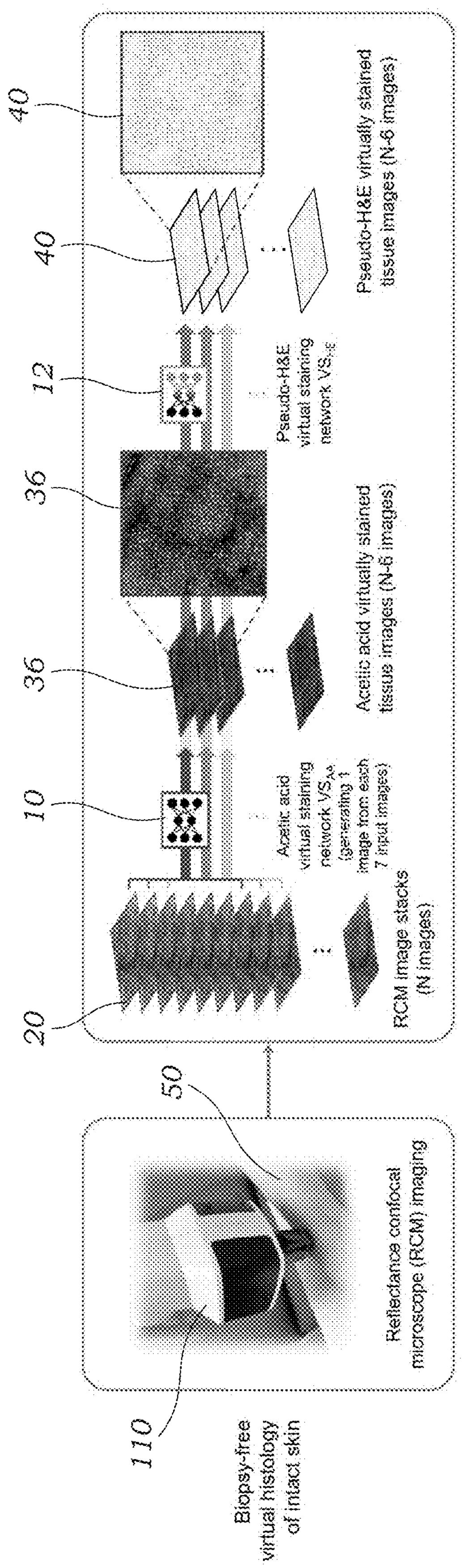
FIG. 1B schematically illustrates the workflow for biopsy-free virtual histological staining procedures for skin pathology. By employing the trained deep neural network that takes a stack of RCM images of unstained intact skin as input and instantly generates corresponding virtually stained tissue images, the reported deep learning based virtual histology of skin may provide a unique avenue to biopsy-free, label-free clinical dermatological diagnosis. In one embodiment, a stack of seven axially adjacent RCM images is fed into a trained deep neural network $VS_{AA}$ and transformed into an acetic acid virtually stained tissue image that is corresponding to the central image of the input stack, so that a stack of N images can be used to generate N−6 virtually stained 3D output images that are axially adjacent. Following this acetic acid virtual staining, a pseudo-H&E virtual staining step is further performed by a trained deep neural network ($VS_{HE}$).

Training of virtual staining networks for in vivo histology of unstained skin. Traditional biopsy requires cleansing and local anesthesia of the skin, followed by surgical removal, histological processing, and examination by a trained physician in histopathological assessment, typically using H&E staining. Through the combination of two sub-components. i.e., hematoxylin and eosin, this staining method is able to stain cell nuclei blue and the extracellular matrix and cytoplasm pink, so that clear nuclear contrast can be achieved to reveal the distribution of cells, providing the foundation for the evaluation of the general layout of the skin tissue structure. As described herein, a new approach using deep learning-enabled transformation of label-free RCM images 20 into H&E-like output images 40 is shown, without the removal of tissue or a biopsy. FIG. 1B schematically illustrates the exemplary workflow that is used to generate the output images 40. Current standard formats of RCM imaging of skin include obtaining stacks of images through different layers of the skin and obtaining a mosaic image through one of the layers of skin. It is believed that the combination of these two formats could provide abundant information input for 3D skin virtual histology. However, obtaining H&E images of the same skin tissue to establish the ground truth for network training is a major challenge. Directly using the brightfield microscopy images of the histochemically stained (H&E) tissue slides after biopsy as the ground truth is simply not feasible, because H&E staining requires a series of operations, including biopsy, sectioning and chemical processing, all of which bring severe deformations to the tissue structure and create major difficulties in aligning the H&E-stained tissue images with the in vivo RCM images of the unstained skin. Furthermore, direct in vivo RCM imaging of unstained skin is unable to provide the demanded nuclear contrast at the input of the network.

Here, acetic acid was used to quickly stain the ex vivo skin tissue in RCM imaging, bringing nuclear contrast to serve as the ground truth. The training experiments were performed accordingly and took time-lapsed RCM videos in the process of acetic acid staining, through which the 3D image sequences were obtained with feature positions traceable before and after the acetic acid staining. According to these sequences, a rough registration of the images 20 was initially performed before and after staining, which was followed by two more rounds of deep learning-based fine image registration processes to obtain accurately registered image stacks (see FIGS. 7A-7D).

Figure 7A:
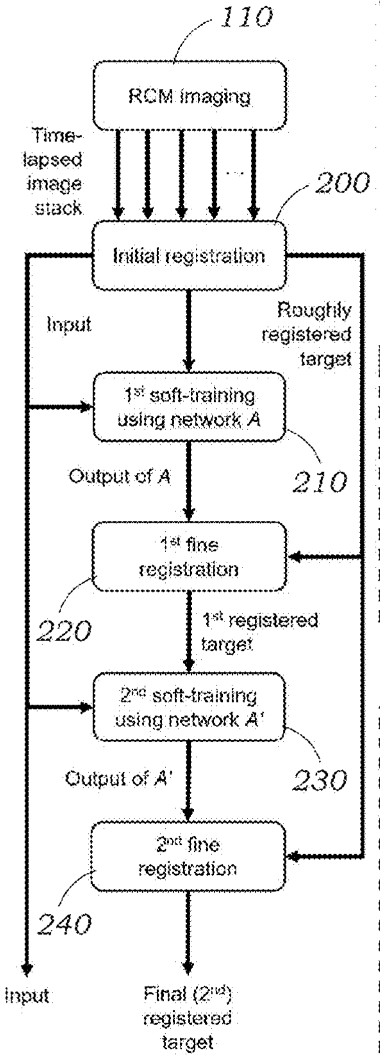
FIGS. 7A-7D illustrates the image registration process for generating input-target image pairs for the training phase of the neural network.
Figure 7B:
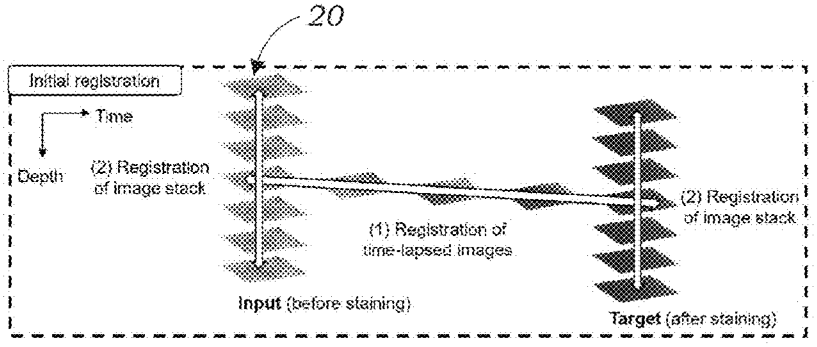
Figure 7C:
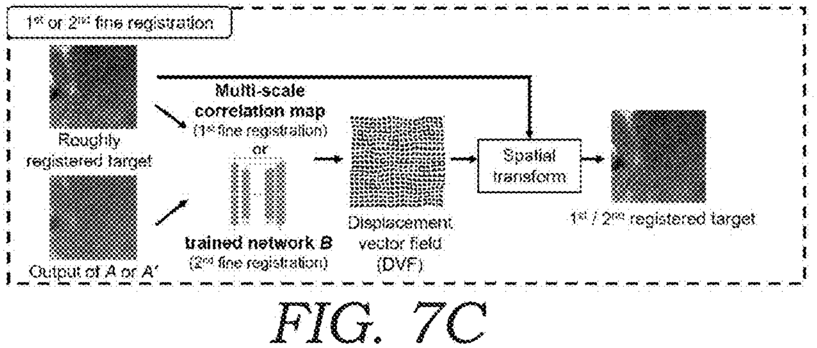
Figure 7D:
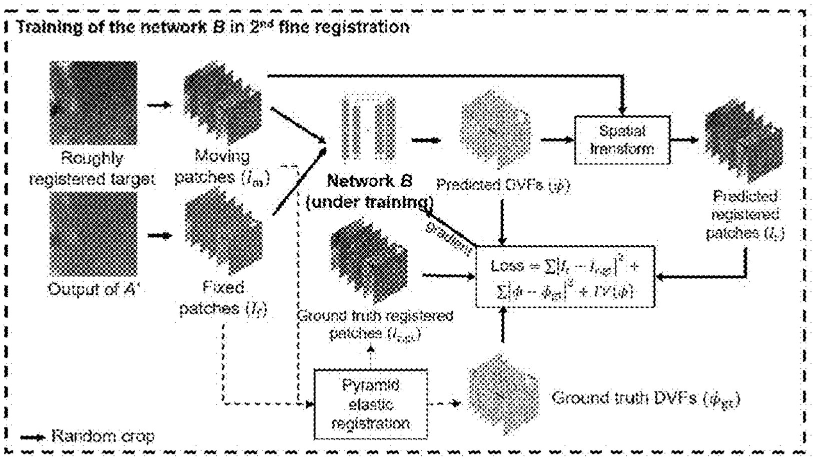

FIG. 7A illustrates a RCM microscope 110 obtaining a time-lapsed image stack. These images 20 are then subject to a first initial registration process as seen in operation 200 of FIG. 7A. A first soft-training is performed using network A (operation 210). The output of network A then is subject to a first fine registration operation 220. The first registered target is then subject to a second soft-training that is performed by network A' as seen in operation 230. This generates output A' that is subject to a second fine registration operation 240 that creates the final ($2^{nd}$) registered target. FIG. 7B illustrates the initial registration operation 200. FIG. 7C illustrates schematically the first or second fine registration operations 220, 240. FIG. 7D illustrates training of the network B used in the second fine registration operation 240.

Figures 8A, 8B:
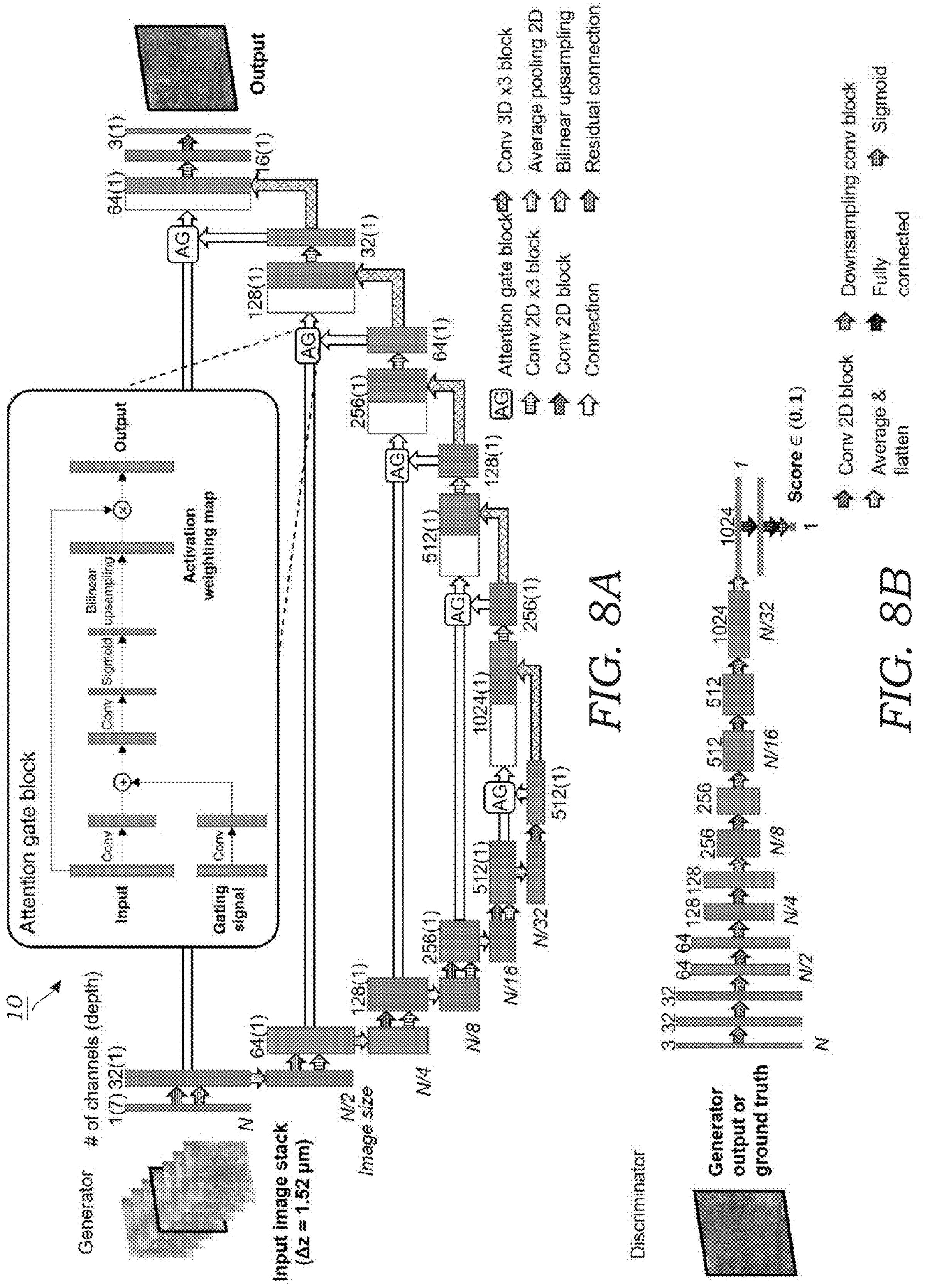
FIGS. 8A-8B illustrates the architecture of the GAN-based deep neural network used for generating images of tissue digitally stained with acetic acid.

These registered image stacks 20 were then used for the training of the acetic acid virtual staining network 10 named $VS_{AA}$, where attention gate modules and 3D convolutions are employed to enable the network to better process 3D spatial structure of tissue (see FIGS. 8A-8B). For generating the in vivo image stack with acetic acid virtual staining, for each inference, $VS_{AA}$ 10 takes a stack of seven (7) axially-adjacent RCM images 20 of horizontal cross-sections of unstained skin tissue 50 and outputs the virtually stained tissue image 36 that is corresponding to the central image of the input stack, which forms a "7-to-1" image transformation (see FIG. 1B). Based on this scheme, by processing all the N input RCM images 20 in the input stack, the network $VS_{AA}$ 10 generates a virtually stained 3D image stack that is composed of N−6 output images 36. $VS_{AA}$ 10 was trained using the aforementioned registered image stacks with a training set composed of 1185 input/output image pairs, and also transformed the acetic acid virtual staining results into H&E-like images using another, trained deep neural network, named pseudo-H&E virtual staining network: $VS_{HE}$ 12 (see FIG. 1B). Additional details about the image registration process, network structure, and the training details of acetic acid and pseudo-H&E virtual staining networks (i.e., $VS_{AA}$ 10 and $VS_{HE}$ 12, respectively) can be found in the Methods section herein.

Figure 2A:
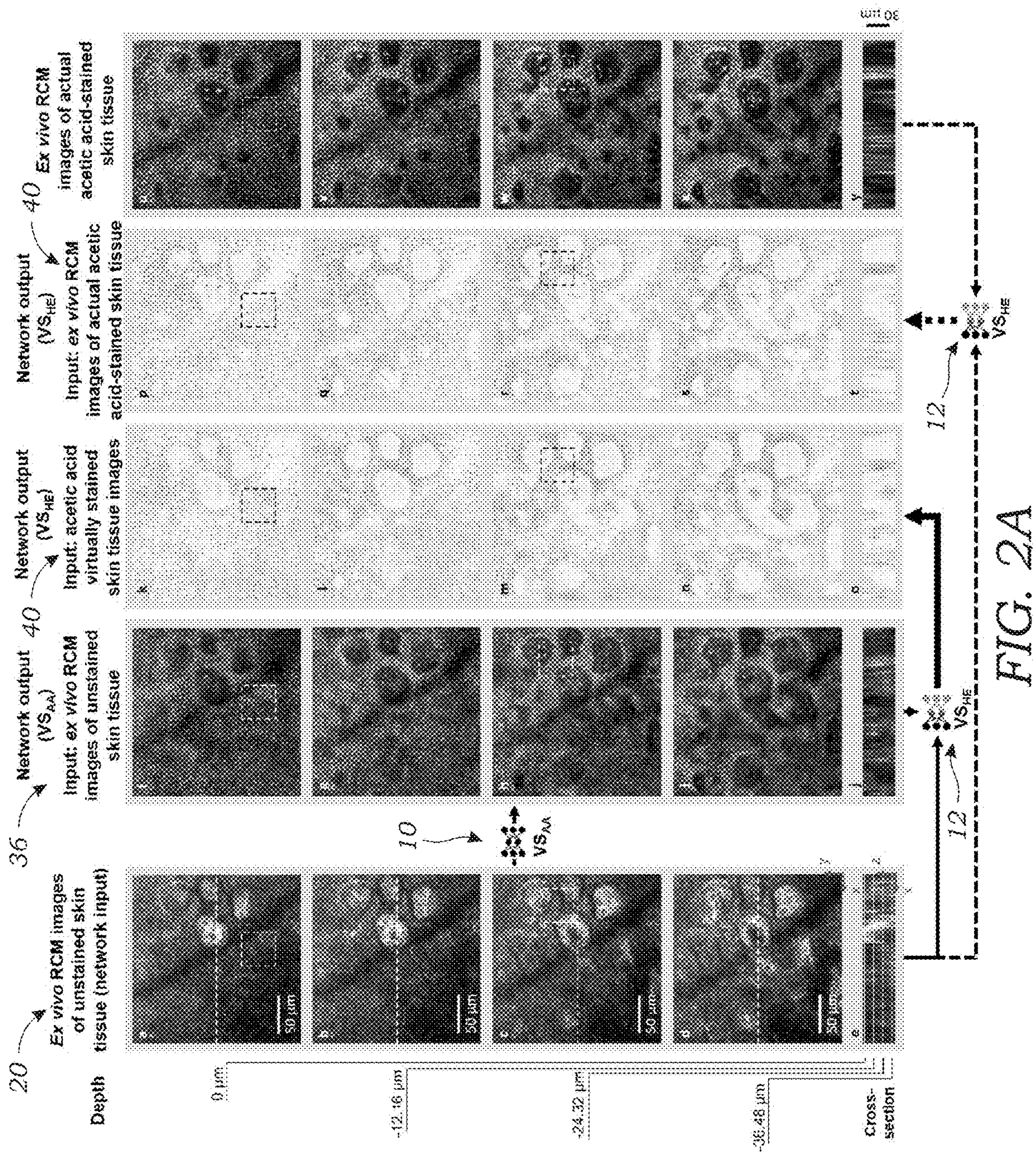
FIG. 2A illustrates the 3D ex vivo virtual staining results of a skin tissue area around dermal-epidermal junction and their comparison with ground truth, actual acetic acid staining. Images in panels a-d are label-free RCM images showing an ex vivo skin tissue area at different depths around dermal-epidermal junction without any staining, served as the network inputs. The depth of (b), (c) and (d) were 12.16, 24.32 and 36.48 μm below (a) into the skin, respectively. Image panel (e) is a cross-section of the RCM image stack of the tissue area including (a)-(d). Lines (left) are used to indicate the depth positions of (a)-(d). Image panels (f)-(i) are acetic acid virtual staining results of the same tissue area and depth as (a)-(d) generated by the deep neural network $VS_{AA}$. Image panel (j) is the image stack cross-section of the acetic acid virtual staining results including (f)-(i) generated using the acetic acid virtually stained tissue images. Image panels (k)-(n) are pseudo-H&E virtual staining results generated using the acetic acid virtually stained tissue images (f)-(i). These H&E-like images were generated by the pseudo-H&E virtual staining network $VS_{HE}$ that took both the RCM images of the unstained tissue (a)-(d) and acetic acid virtually stained tissue images (f)-(i) as input (see solid arrows at the bottom). Image panel (o) is a cross-section of the pseudo-H&E virtually stained tissue image stack including (k)-(n). Image panels (u)-(x) are RCM images of the same tissue area and depth as (a)-(d) after actual acetic acid staining process, served as ground truth for (f)-(i). Image panel (y) shows the cross-section of image stack of the tissue stained with acetic acid including (u)-(x). Image panels (p)-(s) are pseudo-H&E virtual staining results generated using the actual acetic acid-stained images (u)-(x). These H&E-like images were generated by the same pseudo-H&E virtual staining network $VS_{HE}$ that took the RCM images of the unstained tissue (a)-(c) and actual acetic acid-stained images (q)-(s) as input (see dashed arrows at the bottom, and see Methods for more details). Image panel (t) shows the cross-section of the pseudo-H&E virtually stained tissue image stack including (p)-(s) generated using the actual acetic acid-stained images.
Figure 2B:
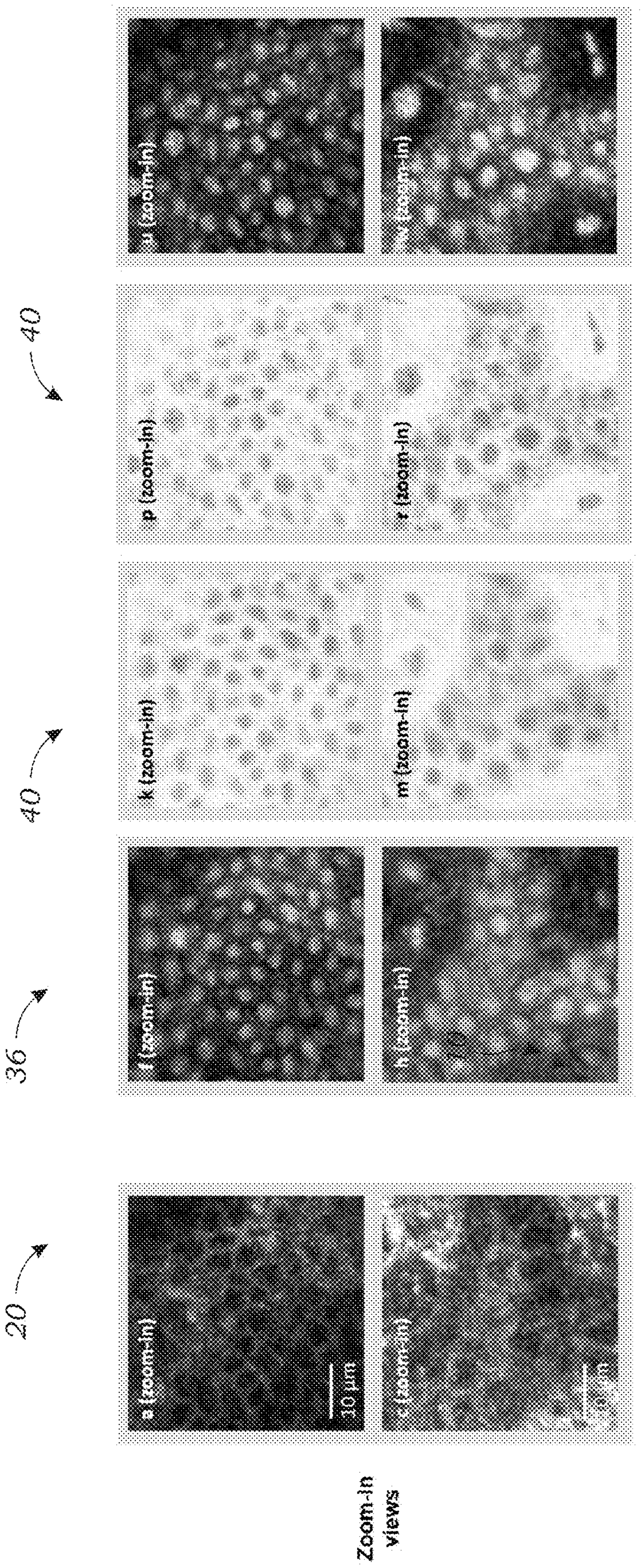
FIG. 2B illustrates zoomed-in views obtained from the dashed regions in image panels (a), (c), (f), (h), (k), (m), (p), (r), (u), and (w) of FIG. 2A.
Figure 9A:
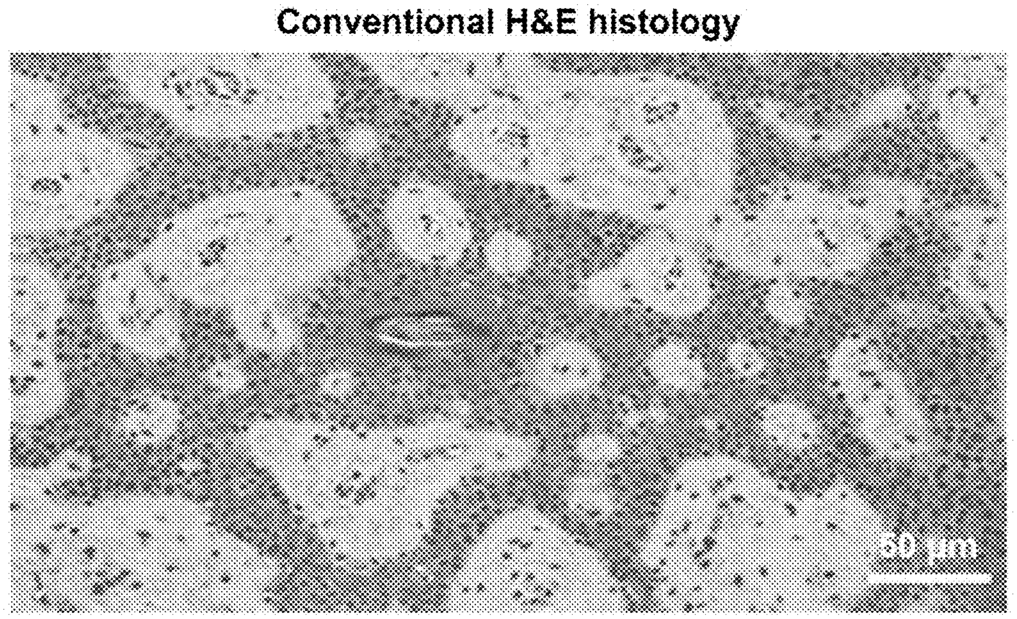
FIGS. 9A-9B illustrate histology image examples for comparison.
Figure 10A:
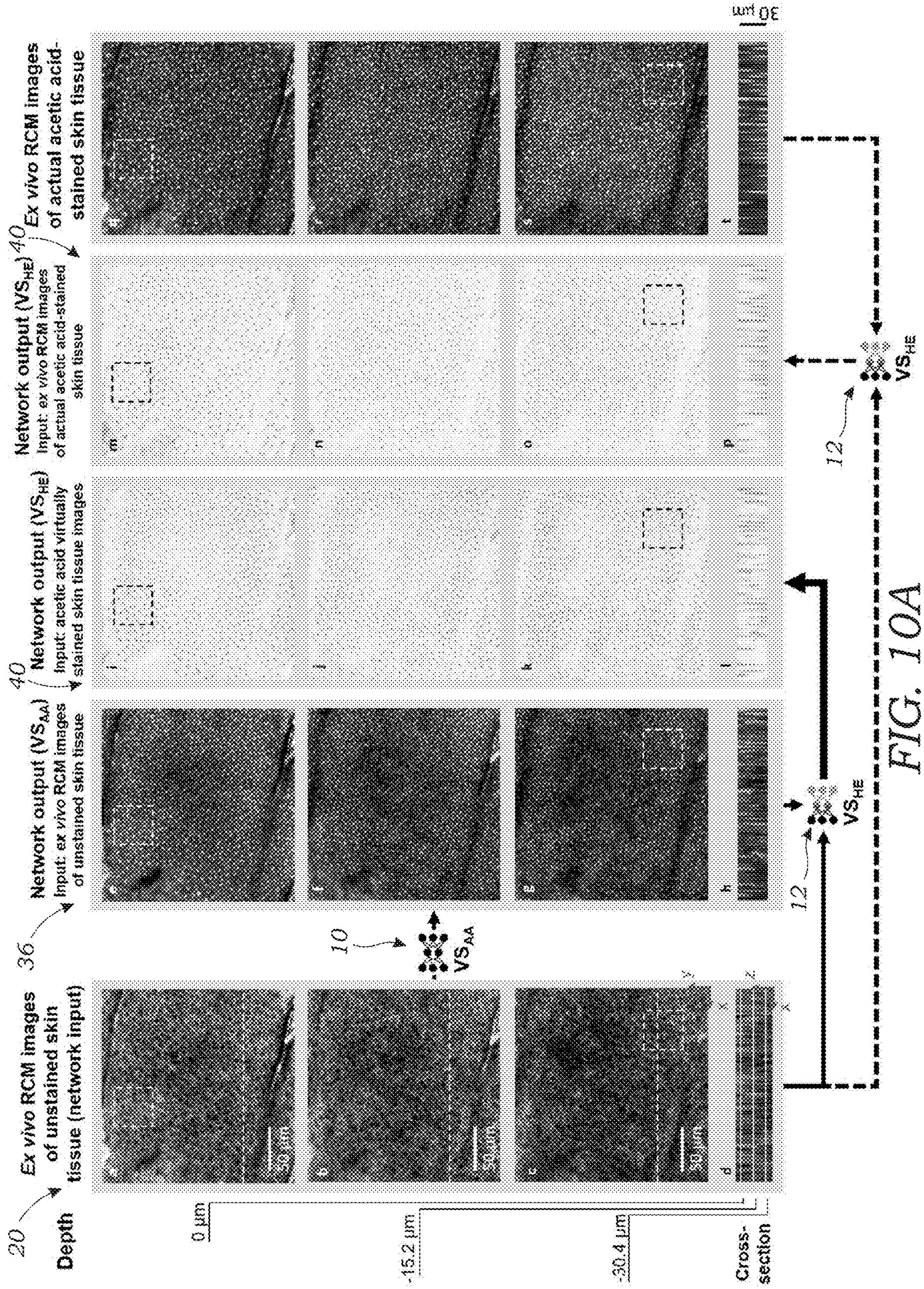
FIG. 10A illustrates 3D ex vivo virtual staining results of normal skin tissue and comparison with ground truth with actual acetic acid staining. Image panels (a)-(c) are label-free RCM images showing an ex vivo normal skin tissue area at different depths without any staining, which serve as the network inputs. The axial depths of image panels (b) and (c) were 15.2 and 30.4 μm below the depth of (a), into the skin, respectively. Image panel (d) is a cross-section of the RCM image stack of the tissue area including (a)-(c). Lines (left) are used to indicate the depth positions of image panels (a)-(c). Image panels (e)-(g) are acetic acid virtual staining results of the same tissue areas and depths as in (a)-(c) generated by $VS_{AA}$. Image panel (h) is the image stack cross-section of the acetic acid virtual staining results including image panels (e)-(g). Image panels (i)-(k) are pseudo-H&E virtual staining results generated using the acetic acid virtually stained tissue images of image panels (e)-(g). These H&E images were generated by $VS_{HE}$ that took both the RCM images of the unstained tissue (a)-(c) and acetic acid virtually stained tissue images of image panels (e)-(g) as input (see solid arrows at the bottom). Image panel (l) is a cross-section of the pseudo-H&E virtually stained tissue image stack including (i)-(k) generated using the acetic acid virtually stained tissue images. Image panels (q)-(s) are RCM images of the same tissue area and depth as in (a)-(c) after actual acetic acid staining process, which serve as ground truth for image panels (e)-(g). Image panel (t) shows the cross-section of the image stack of the tissue stained with acetic acid including image panels (q)-(s). Image panels (m)-(o) are pseudo-H&E virtual staining results generated using the actual acetic acid-stained tissue images of image panels (q)-(s). These H&E images were generated by the same $VS_{HE}$ that took the RCM images of the unstained tissue (a)-(c) and actual acetic acid-stained images (q)-(s) as input (see dashed arrows at the bottom, and see Methods section, for details). Image panel (p) shows the cross-section of pseudo-H&E virtually stained tissue image stack including image panels (m)-(o) generated using the actual acetic tissue acid-stained images.
Figure 10B:
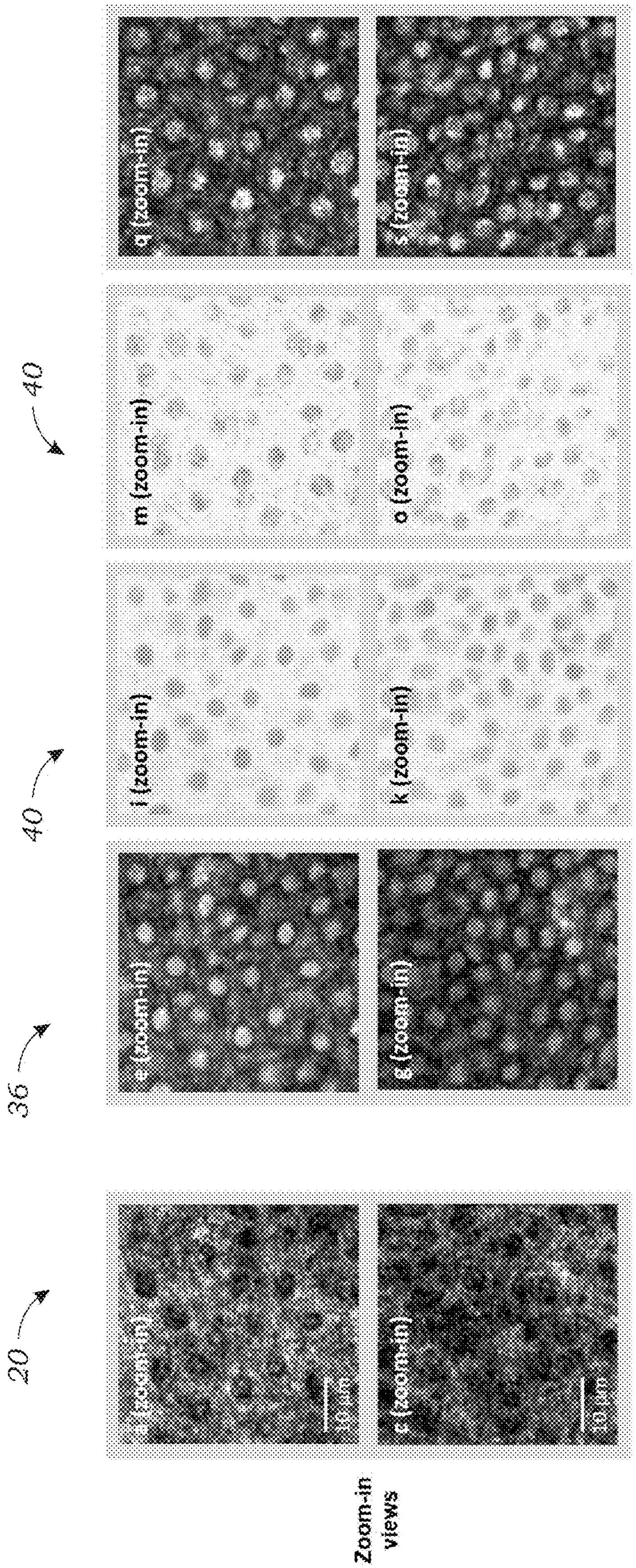
FIG. 10B illustrates zoomed-in views obtained from the dashed regions in image panels (a), (c), (e), (g), (l), (k), (m), (o), (q), and (s) of FIG. 10A.

Virtual staining of RCM image stacks of normal skin samples ex vivo. Staining of skin blocks with acetic acid allowed the visualization of nuclei from excised tissue at the dermal-epidermal junction and superficial dermis in normal skin samples. Using these images as the ground truth (only for comparison), first it was tested whether the RCM images 20 of unstained tissue can be transformed into H&E-like images 40 using the deep learning-based virtual histology method. The data, summarized in FIGS. 2A-2B (image panels a-y in FIGS. 2A, 2B), demonstrate that cross-sections of RCM image stacks taken at various depths around the dermal-epidermal junction of a skin lesion could be transformed into virtually stained tissue images 40 with inferred nuclei, showing good correspondence with the actual acetic acid-stained RCM images used for ground truth comparison. Furthermore, pseudo-H&E virtual staining was performed using these acetic acid-stained image results (see FIGS. 2A-2B). An example of traditionally processed skin histology through the dermal-epidermal junction in the horizontal plane is also shown in FIG. 9A to illustrate the visual similarity of virtually stained tissue image 40 shown in FIGS. 2A-2B. The acetic acid virtual staining network $VS_{AA}$ 10 performed similarly well when ex vivo image stacks of the spinous layer of the epidermis were utilized as input, as shown in FIGS. 10A-10B (image panels a-t).

Figures 3A, 3B, 3C:
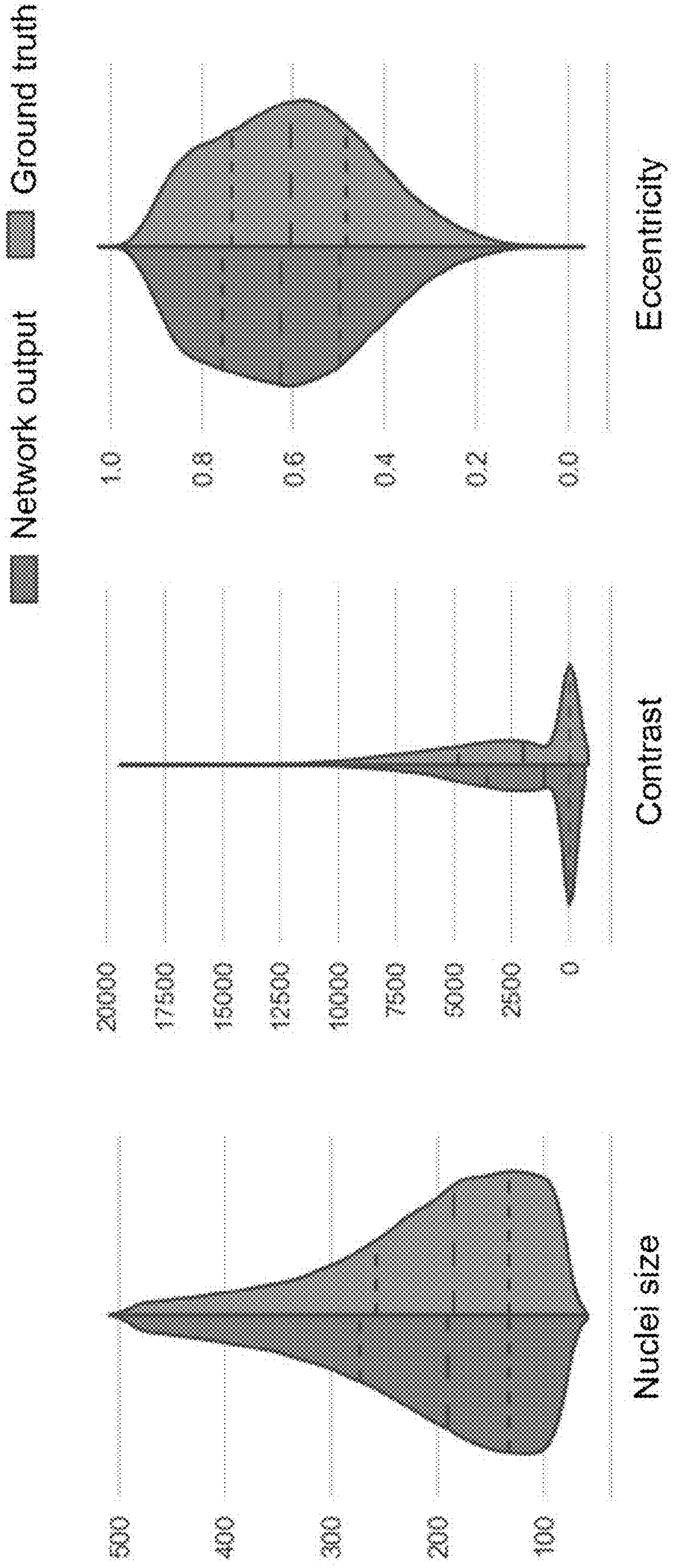
FIGS. 3A-3G: Quantitative analysis of the acetic acid virtual staining results on ex vivo skin tissue samples.
Figure 3D:
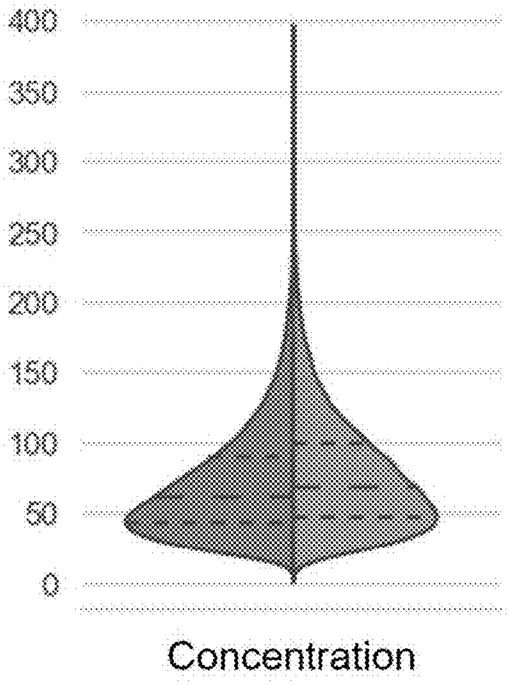
Figure 3E:
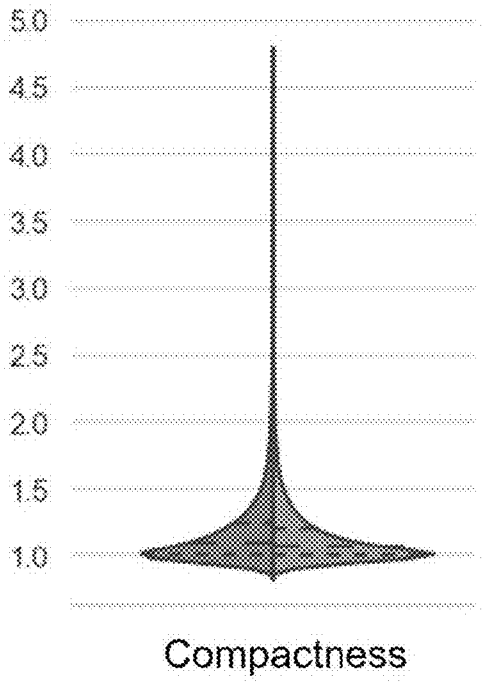
Figure 3F:
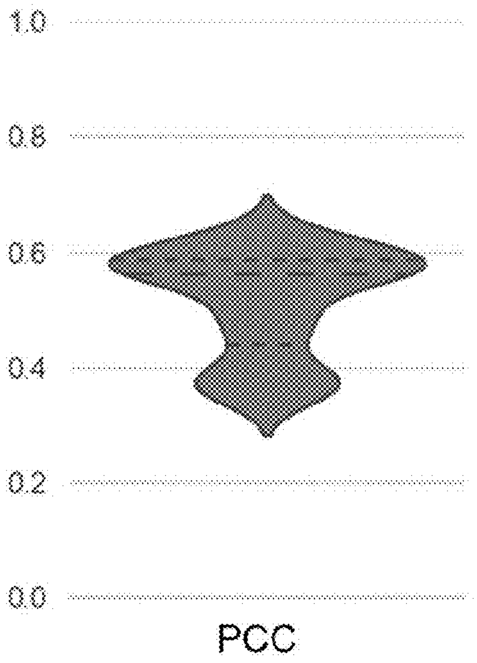
Figure 3G:
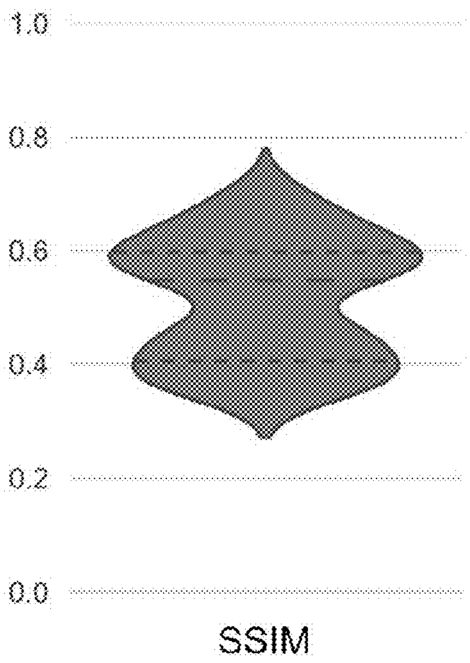
Figure 11:
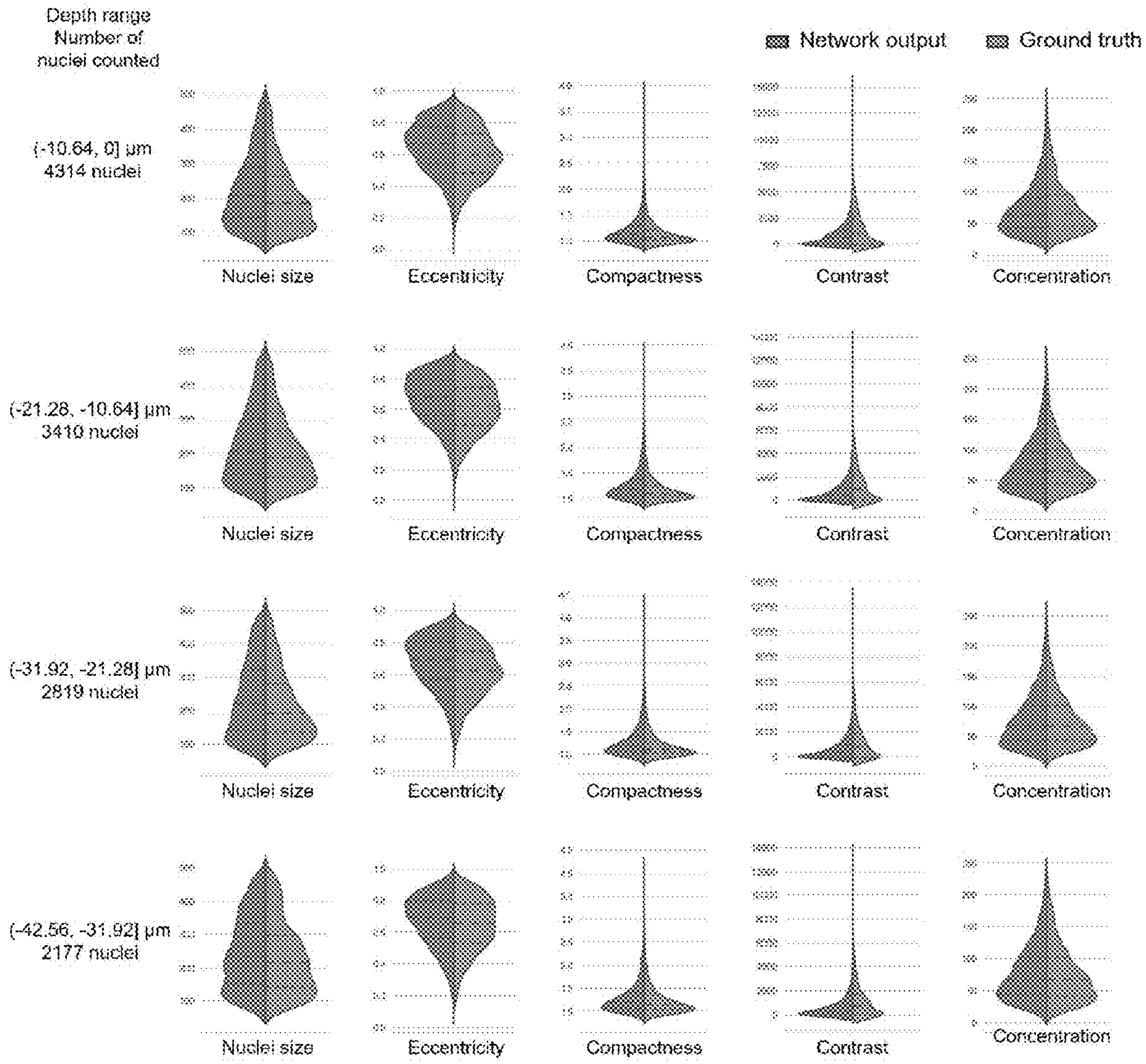
FIG. 11: Quantitative morphological analysis of the 3D virtual staining results using the ex vivo skin tissue area shown in FIG. 2A. The violin plots show comparisons of the statistical distributions of the nuclear morphological profiles between the acetic acid virtually stained skin tissue images (network output) and their corresponding ground truth obtained using the actual acetic acid staining (ground truth). The image stack is divided into four subsets according to the depth range, each corresponding to one row and covering an axial depth range of 10.64 μm, where statistical analyses were performed individually using five metrics including: nuclei size, eccentricity, compactness, contrast, and concentration. Dashed lines in the violin plots from top to bottom represent the 75%, 50% (median) and 25% quartile, respectively. The nuclear object detection was performed using the segmentation algorithm in CellProfiler (see the Methods section for details).

Next, the prediction performance of the model was evaluated through a series of quantitative analyses. To do so, first the acetic acid virtual staining results were generated of the entire ex vivo testing set that contains 199 ex vivo RCM images collected from 6 different unstained skin samples from 6 patients. Segmentation was performed on both the virtual histology images of normal skin samples and their ground truth images to identify the individual nuclei on these images. Using the overlap between the segmented nuclear features of acetic acid virtual staining images and those in the actual acetic acid-stained ground truth images as a criterion, each nucleus in these images was classified into the categories of true positive (TP), false positive (FP) and false negative (FN) and quantified the sensitivity and precision values of the prediction results (see the Methods for details). It was found that the virtual staining results achieved ~80% sensitivity and ~70% precision for nuclei prediction on the ex vivo testing image set. Then, using the same segmentation results, the nuclear morphological features in the acetic acid virtual staining and ground truth images were further assessed. Five morphological metrics, including nuclear size, eccentricity, compactness, contrast, and concentration, were measured for this analysis (see Methods for details). As shown in FIGS. 3A-3E, these analyses demonstrate that the statistical distributions of these nuclear morphological parameters calculated using the acetic acid virtual staining results presented a very good match with those of the actual acetic acid-stained ground truth images, regardless of the metrics used. In order to further demonstrate the efficacy of the virtual staining results for three-dimensional imaging, in FIG. 11 the results are reported of the same type of analysis for the image stack used and shown in FIGS. 2A-2B, but this time focusing on different depth ranges within the tissue block: once again, a strong match between the acetic acid virtually stained skin tissue images 36 and their actual acetic acid-stained ground truth is observed for all the quantitative metrics used, regardless of the depth range selected. In addition, to evaluate the results from the perspective of overall image similarity, the Pearson correlation coefficient (PCC) was calculated of each image pair composed of acetic acid virtual staining results and the ground truth in the ex vivo testing image set. The results of these PCC and SSIM analysis are shown in FIGS. 3F and 3G, where the median PCC and SSIM values are found to be 0.561 and 0.548, respectively.

Figure 4A:
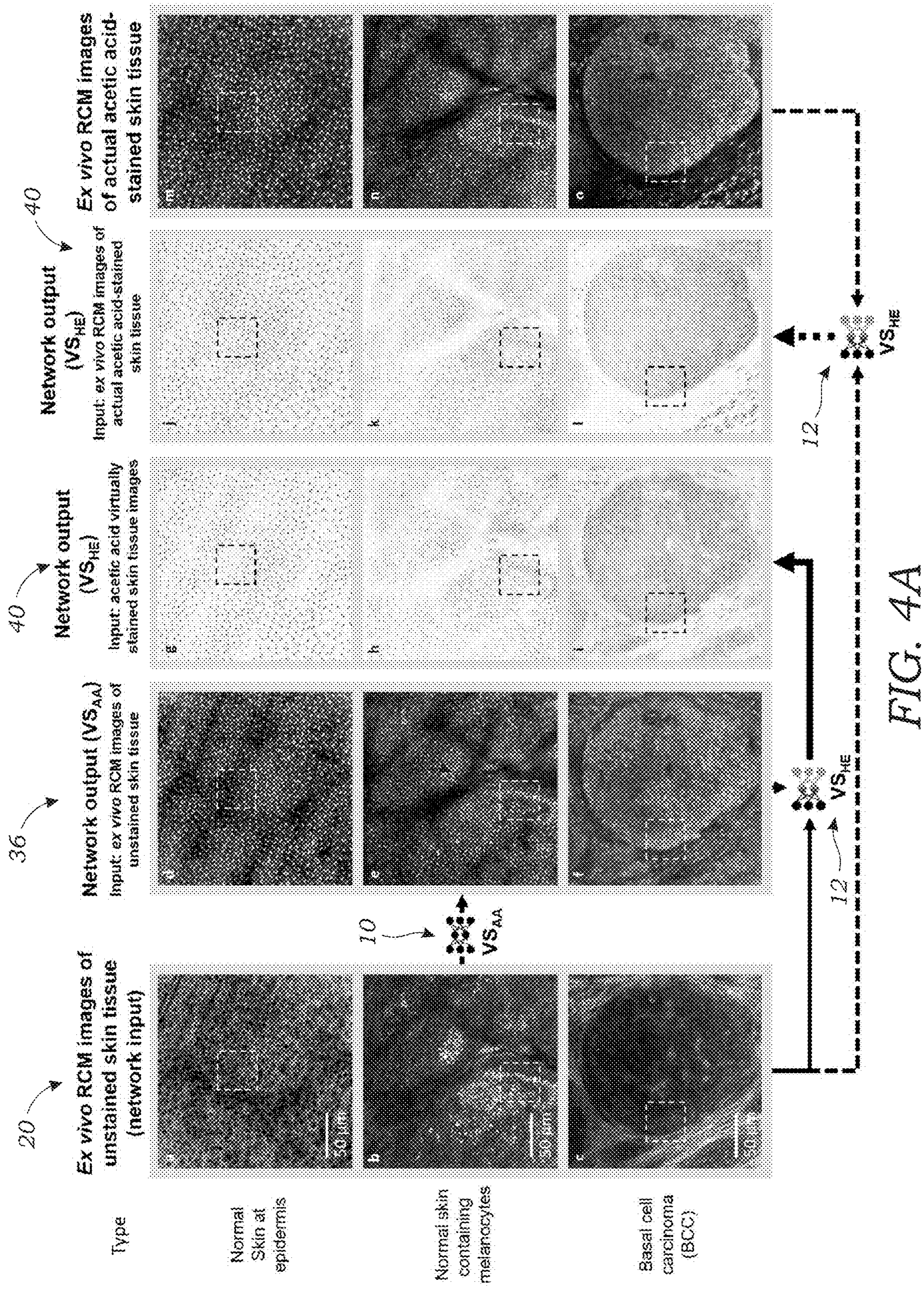
FIG. 4A illustrates virtual staining results for different types of ex vivo skin tissue areas and their comparison with ground truth, actual acetic acid staining. Image panels (a)-(c) are label-free RCM images of three different types of ex vivo skin tissue areas, including (a) normal skin, (b) a melanocytic nevus and (c) skin containing BCC, which are used as input of the virtual staining neural networks. Image panels (d)-(f) are acetic acid virtual staining results of the same tissue areas in (a)-(c) generated by the deep neural network $VS_{AA}$. Image panels (g)-(i) are pseudo-H&E virtual staining results generated using the acetic acid virtually stained tissue images (d)-(f). These H&E-like images were generated by the pseudo-H&E virtual staining network $VS_{HE}$ that took both the RCM images of the unstained tissue (a)-(c) and the acetic acid virtually stained tissue images (e)-(g) as input (see solid arrows at the bottom). Image panels (m)-(o) show RCM images of the same tissue area and depth as (a)-(c) after the actual acetic acid staining process, which served as ground truth for (d)-(f). Image panels (j)-(l) are pseudo-H&E virtual staining results generated using the actual acetic acid-stained images (m)-(o). These H&E-like images were generated by the same pseudo-H&E virtual staining network $VS_{HE}$ that took the RCM images of the unstained tissue (a)-(c) and the actual acetic acid-stained images (m)-(o) as input (see the dashed arrows at the bottom, and the Methods section for details).
Figure 4B:
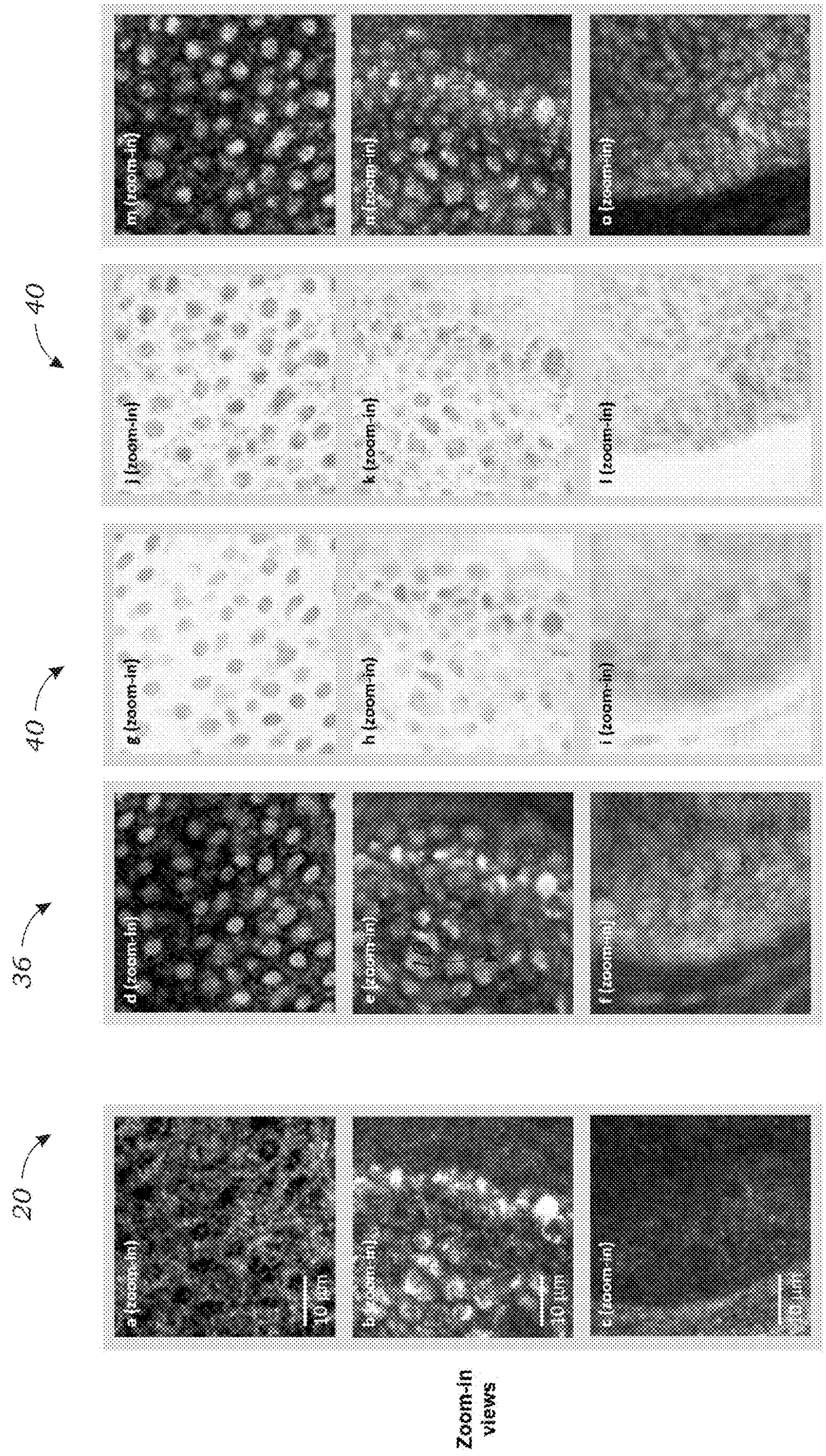
FIG. 4B illustrates zoomed-in views obtained from the dashed regions in image panels (a)-(o) of FIG. 4A.
Figure 9B:
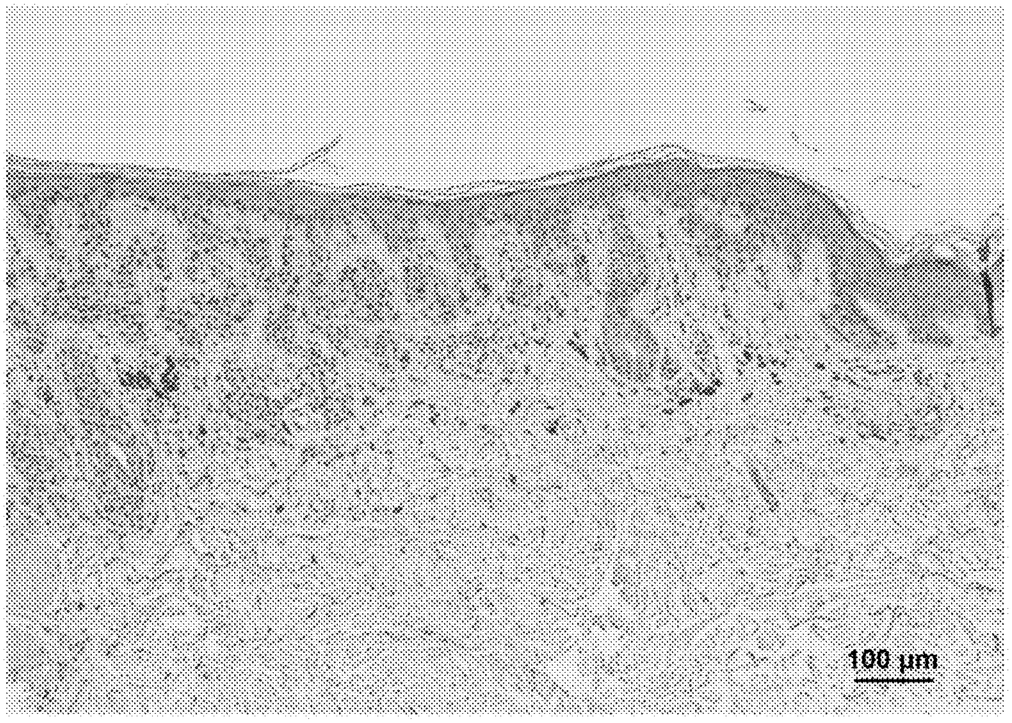

Virtual staining of RCM image stacks of melanocytic nevi and basal cell carcinoma ex vivo. To determine whether the method can be used to assess skin pathology, features seen in common skin neoplasms were imaged. Melanocytes are found at the dermal-epidermal junction in normal skin and increase in number and location in both benign and malignant melanocytic neoplasms. For the approach to be successful, it needs to incorporate pigmented melanocytes in order to be useful for interpretation of benign and malignant melanocytic neoplasms (nevi and melanoma, respectively). Melanin provides strong endogenous contrast in melanocytes during RCM imaging without acetic acid staining. This allows melanocytes to appear as bright cells in standard RCM images 20 due to high refractive index of melanin. Specimens with normal proportions of melanocytes (FIGS. 4A, 4B (image panels a, d, g, j, m—top row) were compared to specimens containing abundant melanocytes, such as benign melanocytic nevi (image panels b, e, h, k, n—middle row). The pseudo-H&E virtual staining algorithm was able to successfully stain melanocytes and provide pigment coloration similar to the brown pigment seen on histologically-stained specimens. An example of histologically-stained skin tissue section image with brown pigment is provided in FIG. 9B.

Unlike melanocytes, basaloid cells that comprise tumor islands in BCC appear as dark areas in RCM images 20. This appearance is due to the high nuclear-to-cytoplasmic ratio seen in malignant cells and the fact that nuclei do not demonstrate contrast on RCM imaging. Further, mucin present within and surrounding basaloid islands in BCC further limits the visualization of tumor islands due to a low reflectance signal. Since many skin biopsies are performed to rule out BCC, it was next determined whether acetic acid staining can provide ground truth for skin samples containing BCC. 50% acetic acid concentration allowed sufficient penetration through the mucin layer to stain nuclei of BCC. Discarded, approximately 2 mm-thick, Mohs surgical specimens diagnosed as BCC were used and RCM imaging was performed without and with acetic acid staining (the latter formed the ground truth). As illustrated in the bottom row of FIGS. 4A, 4B (image panels c, f, i, l, o), the virtual staining results showed strong concordance of features of BCC when compared to these acetic acid-stained ground truth images; common histological features of BCC, including islands of basaloid cells with small, peripherally palisaded nuclei and dark silhouettes, material resembling mucin within the basaloid islands, and separation (retraction) of basaloid islands from the surrounding stroma were visible in the virtually stained RCM images 36, 40 containing BCC as shown in image panels c, f, i, l, and o of FIGS. 4A, 4B.

Figure 12:
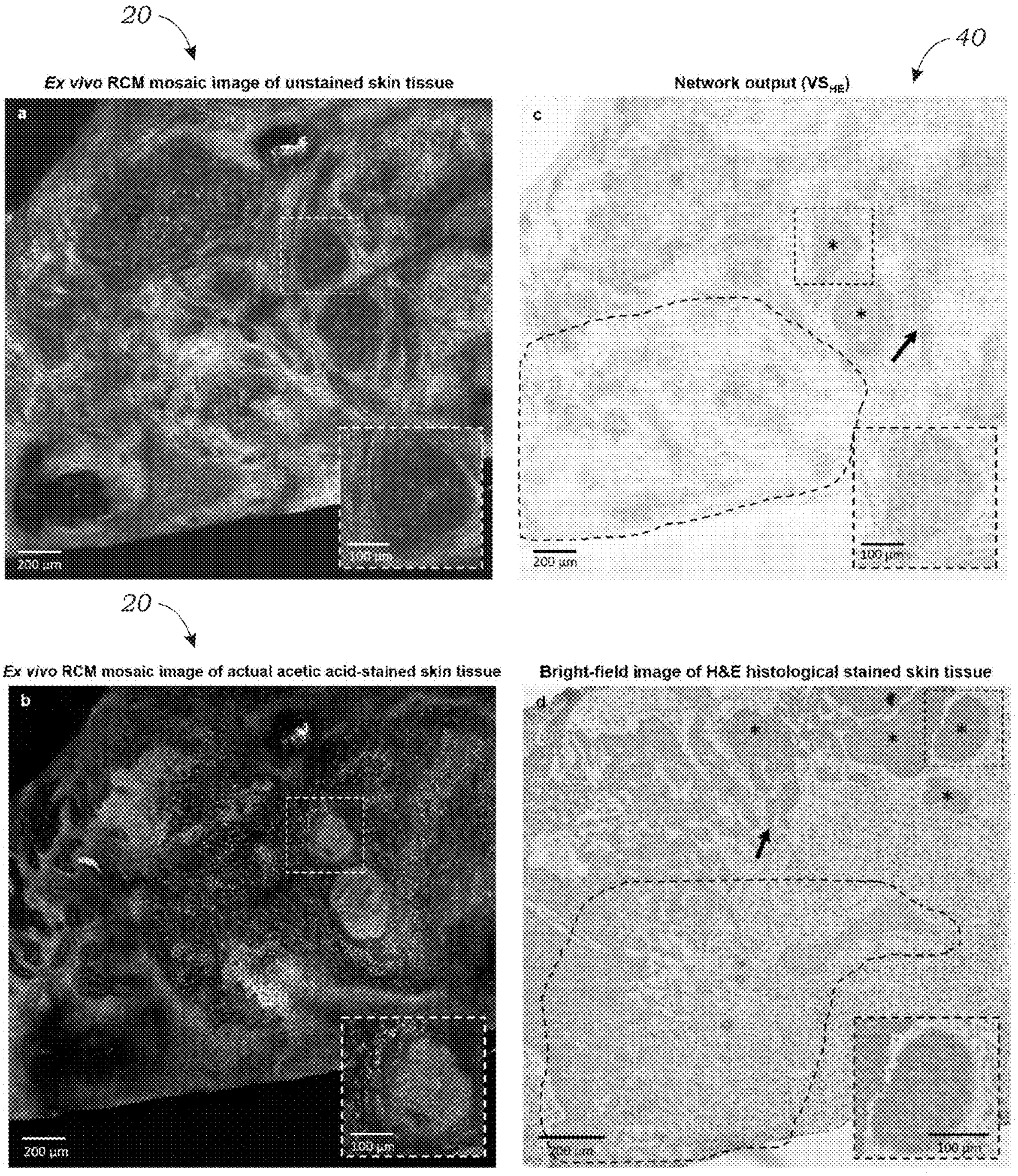
FIG. 12 illustrates pseudo-H&E virtual staining result of a mosaic image of an ex vivo skin lesion containing BCC, compared with mosaic RCM image of the same tissue stained with acetic acid and bright-field H&E image of the same tissue with frozen section histology. Image panel (a) is a large field-of-view RCM image mosaic showing an ex vivo skin lesion containing BCCs. Image panel (b) is a RCM image mosaic of the same tissue lesion in (a) but stained with acetic acid. Image panel (c) is a pseudo-H&E virtual staining result of (a). Image panel (d) is a bright-field image of the same tissue lesion in (a) after the histological H&E staining process. Note that tissue was processed per Mohs micrographic surgery for margin control, which results in tissue to be in a different plane than horizontal or en face in order to visualize the deep and lateral tissue margins simultaneously.

Virtual staining of mosaic RCM images ex vivo. Mosaic images are formed by multiple individual RCM images 20 scanned over a large area at the same depth to provide larger field-of-view of the tissue 50 to be examined for interpretation and diagnosis. To demonstrate virtual staining of mosaic RCM images, ex vivo RCM images 20 of BCC in a tissue specimen 50 obtained from a Mohs surgery procedure were converted to virtual histology. Through visual inspection, the virtual histology image 40 shown in FIG. 12 (image panel c) demonstrated similar features observed in a representative histological section (FIG. 12 (image panel d))—not in the same plane as the RCM images 20 obtained from the actual frozen section histology of the processed tissue. Of note, this tissue specimen 50 used for FIG. 12 displayed both nodular and infiltrative islands of BCC. Since the algorithm was only trained on nodular BCC, it is not surprising that it performed much better at revealing the nodular islands of BCC within the specimen rather than the thin cords of infiltrative BCC displaying some keratinization, although both nodules and thin cords are still visible in the virtually-stained image 40 as shown in FIG. 12 (image panel c).

Figure 5:
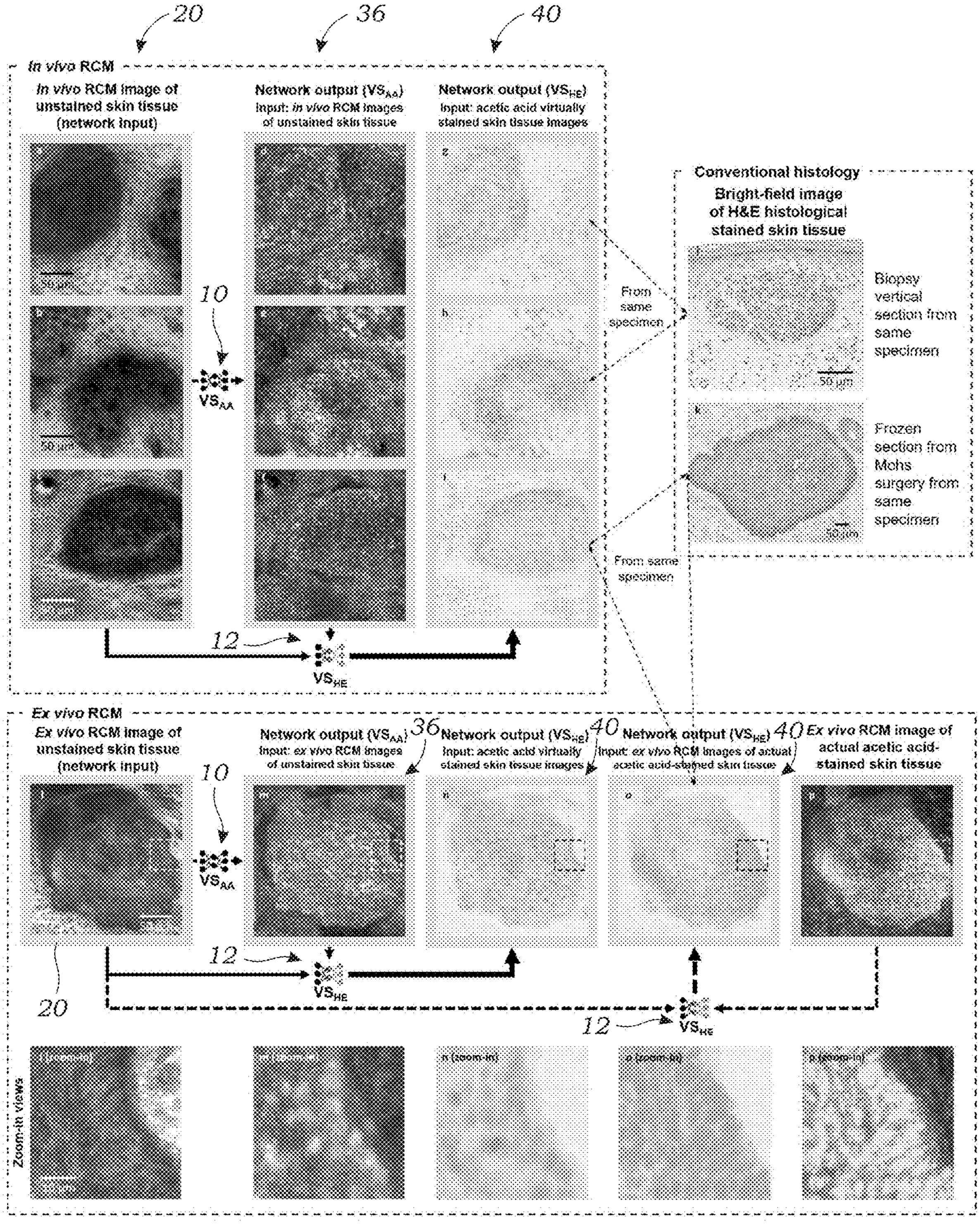
FIG. 5 illustrates virtual staining results of in vivo RCM images of skin tissue areas that contain BCCs. Image panels (a)-(i) are in vivo RCM images of unstained skin, while image panels (j, k) and (l)-(p) are H&E histology and ex vivo RCM images used for comparison, respectively. The trained network $VS_{AA}$ transformed label-free in vivo RCM images of unstained tissue areas with BCCs (a)-(c) as input into their acetic acid virtual staining results as seen in image panels (d-f). Pseudo-H&E virtual staining was further performed by the trained network $VS_{HE}$ to generate the H&E versions of (d)-(f) by taking both the RCM images of the unstained tissue (a)-(c) and the acetic acid virtually stained tissue images of image panels (d)-(f) as input (see arrows at the bottom of the In vivo RCM panel). For comparison with these in vivo virtual staining results, in image panels (j) and (k) bright-field images are shown of visually similar BCC regions taken from same specimen after H&E histochemical staining. Note that these BCC regions in image panels (g)-(i) are not necessarily the same BCC tumor nodule as shown in H&E histology image panels (j)-(k), but are from the same specimen, and may be subject to structural deformations due to the standard histochemical staining and related sample processing. Image panel (j) is the H&E histology of a vertical section biopsy taken from the same specimen used for (g, h), and image panel (k) is the H&E histology of a frozen section from Mohs surgery taken from the same specimen used for in vivo (i) and ex vivo (o). As another comparison, ex vivo acetic acid virtually stained and actual acetic acid-stained results are shown for the same specimen used for image panel (i). The same trained network $VS_{AA}$ was used to transform label-free ex vivo RCM images of unstained tissue areas with BCCs (l) into ex vivo acetic acid virtually stained tissue images shown in image panel (m), forming a comparison with the ground truth images of the same tissue area actually stained with acetic acid of image panel (p). The same pseudo-H&E virtual staining was also applied to image panels (m, p) using the network $VS_{HE}$ to generate their pseudo-H&E virtually stained counterparts of image panels (n, o) (see the arrows at the bottom of the orange Ex vivo RCM panel, and see the Methods for details). Corresponding zoomed-in regions from image panels (i), (m), (n), (o), and (p) are illustrated respectively, below each of these non-zoomed image panels in FIG. 5.
Figure 13:
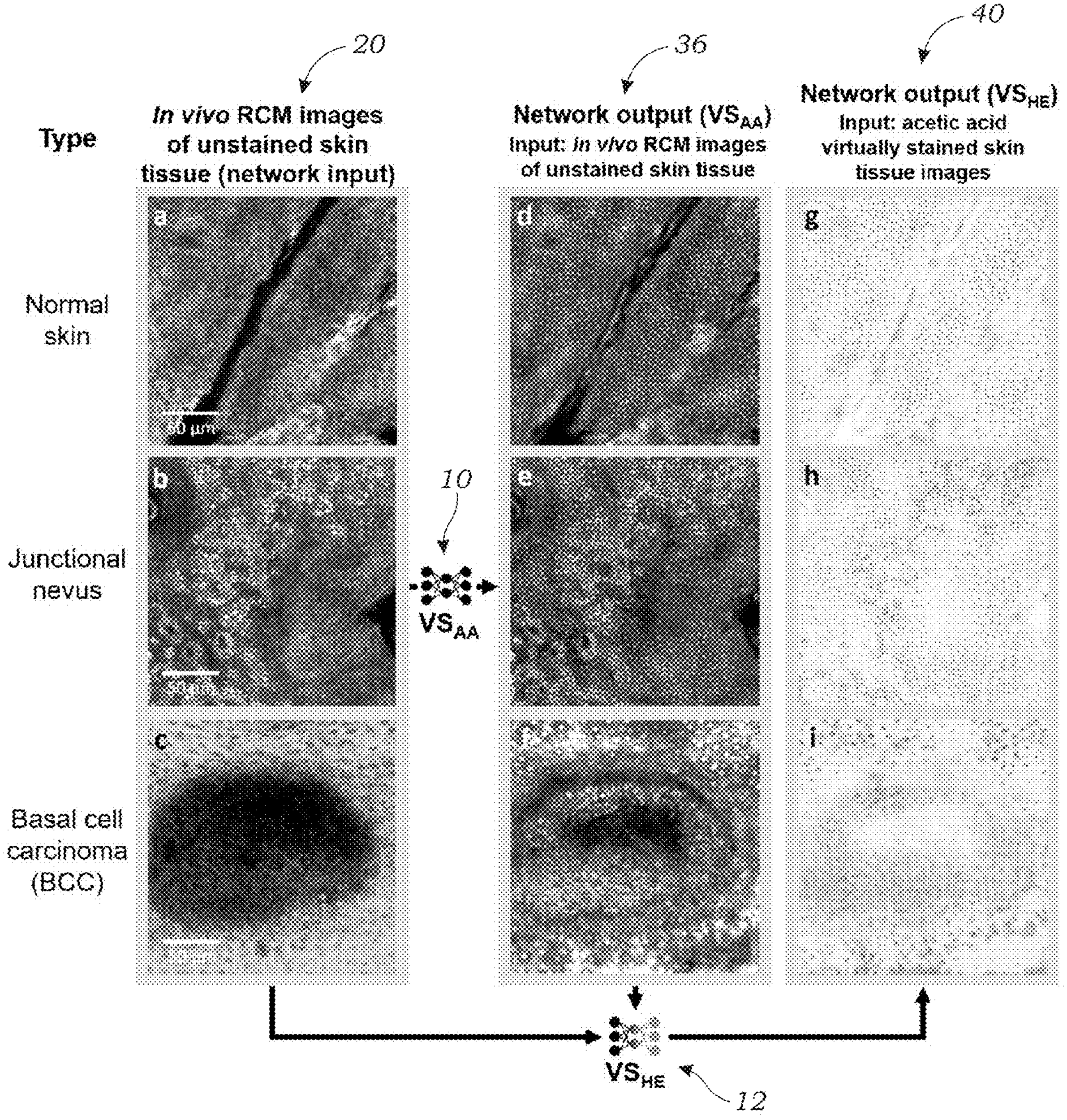
FIG. 13 illustrates virtual staining results for different types of n vivo skin tissue areas. Image panels (a)-(c) are label-free RCM images of three different types of in vivo skin tissue areas, including (a) normal skin, (b) junctional nevus containing melanocytes and (c) skin containing basal cell carcinoma (BCC), which are used as the network inputs. Image panels (d)-(f) are acetic acid virtual staining results of the same tissue areas in (a)-(c) generated by the deep neural network $VS_{AA}$. Image panels (g)-(i) are pseudo-H&E virtual staining results generated using the acetic acid virtually stained tissue images of image panels (d)-(f). These H&E images were generated by the virtual staining network $VS_{HE}$ that took both the RCM images of the unstained tissue of image panels (a)-(c) and the acetic acid virtually stained tissue images of image panels (d)-(f) as input (see the arrows at the bottom, and the Methods section for details).
Figure 14:
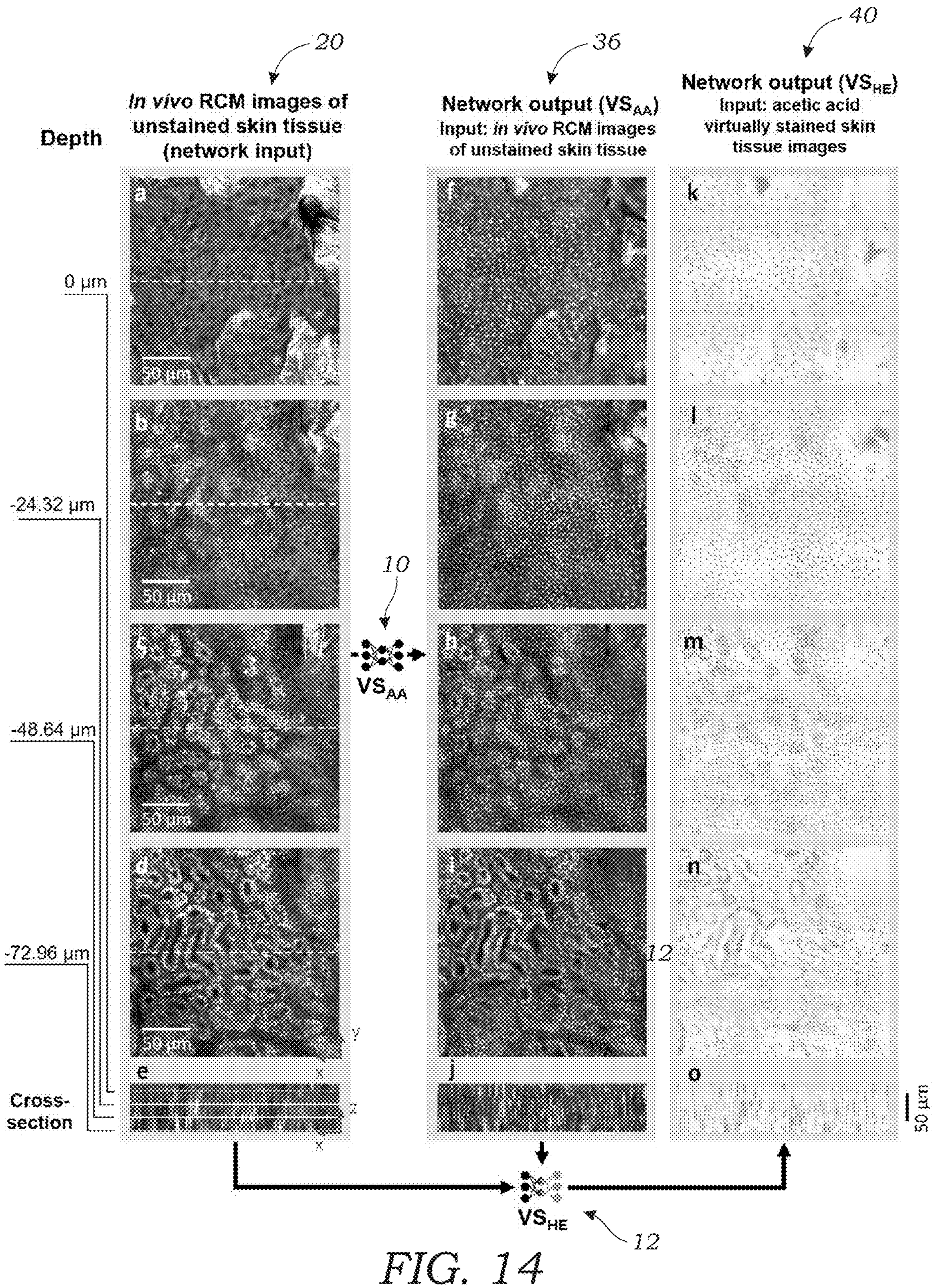
FIG. 14 illustrates 3D in vivo virtual staining results of skin tissue. Image panels (a)-(d) are label-free RCM images showing an in vivo skin tissue area at different depths without any staining, serving as the network inputs. The depths of image panels (b), (c) and (d) were 24.32, 48.64 and 72.96 μm below the depth of (a), into the skin, respectively. Image panel (e) is a cross-section of the RCM image stack of the tissue area including image panels (a)-(d). Lines (left) are used to indicate the depth positions of image panels (a)-(d). Image panels (f)-(i) are acetic acid virtual staining results of the same tissue area and depth as in image panels (a)-(d) generated by $VS_{AA}$. Image panel (j) is the image stack cross-section of the acetic acid virtual staining results including image panels (f)-(i). Image panels (k)-(n) are pseudo-H&E virtual staining generated using the acetic acid virtually stained tissue images of image panels (f)-(i). These H&E images were generated by the virtual staining network $VS_{HE}$ that took both the RCM images of the unstained tissue (a)-(d) and the acetic acid virtually stained tissue images (f)-(i) as input (see arrows at the bottom, and the Methods section for details). Image panel (o) is a cross-section of the pseudo-H&E virtually stained tissue image stack including image panels (k)-(n) generated using the acetic acid virtually stained tissue images.

Virtual staining of in vivo image stacks and mosaic RCM images. Next, it was tested whether RCM images 20 of unstained skin obtained in vivo can give accurate histological information using the trained neural network. In vivo RCM images 20 of lesions that are suspicious for BCC were compared to (1) histology from the same lesion obtained following biopsy or Mohs section histology and (2) images obtained ex vivo with acetic acid staining (ground truth). As summarized in FIG. 5 (image panels a-p), virtual staining of in vivo RCM images 40 (image panels g, h, i) again demonstrated features compatible with BCC tumor islands commonly seen on histologically processed and stained tissue (image panels j and k). These results were further confirmed with the ex vivo RCM image of the actual acetic acid-stained tissue of the same lesion (image panels o and p). The virtual histology output image 40 from the trained algorithm using the in vivo images 20 of the skin lesion displayed similar basaloid tumor islands as those seen in the actual acetic acid-stained ex vivo RCM images and the actual histology. Other examples of in vivo stacks of RCM images 36, 40 of normal skin, a junctional nevus, and another BCC sample are presented in FIG. 13 (image panels a-i). The junctional nevus showed expansion of melanocytic cells at the dermal-epidermal junction in a benign ringed pattern. One plane of the image stack is shown for these samples. Another sample, reported in FIG. 14 (image panels a-o), shows various planes of a confocal stack of images 36, 40 of a junctional nevus through all of the skin layers including the granular layer ($1^{st}$ row), spinous layer ($2^{nd}$ row), basal layer ($3^{rd}$ row), and dermal-epidermal junction ($4^{th}$ row).

Figure 6:
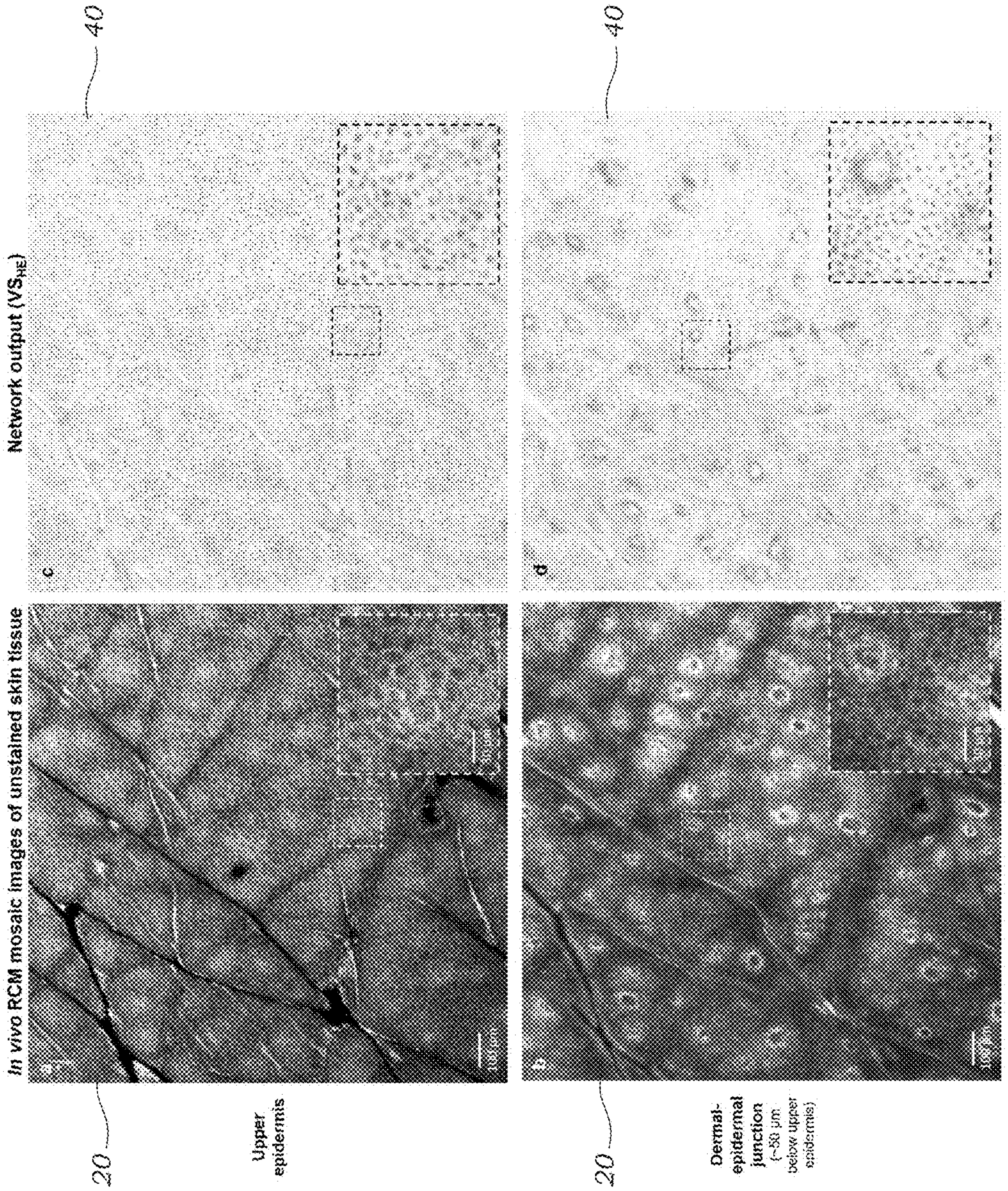
FIG. 6 illustrates pseudo-H&E virtual staining results of large field-of-view mosaic images of an in vivo skin tissue at two different depths. Image panels (a) and (b) are label-free in vivo RCM image mosaics at two cross-sections corresponding to (a) upper epidermis and (b) dermal-epidermal junction. The axial gap between the two cross-sections is around 50 μm. Image panels (c) and (d) are pseudo-H&E virtual staining results of (a) and (b), respectively.

It was also examined whether the virtual staining method can be applied to mosaic in vivo RCM images, despite the fact that the network 10, 12 was not trained on a full set of mosaic images. These mosaic RCM images 40 are important because they are often used in clinical settings to extend the field-of-view for interpretation and are required for the reimbursement of the RCM imaging procedure. The results reported in FIG. 6 reveal that in vivo mosaic images of unstained skin tissue, through the spinous layer of the epidermis and the dermal-epidermal junction, were successfully transformed into H&E-like images 40 without acetic acid staining. These results confirm that the virtual staining network 10, 12 trained on confocal image stacks was able to perform virtual in vivo histology of RCM image stacks of common skin lesions, including BCC and nevus, as well as large mosaic RCM images of normal skin without the need for further training.

Finally, the inference speed of the trained deep network models 10, 12 were tested using RCM image stacks, and demonstrated the feasibility of real-time virtual staining operation (see Methods for details). For example, using eight Tesla A100 GPUs to perform virtual staining through $VS_{AA}$ 10 and $VS_{HE}$ 12 networks, the inference time for an image size of 896×896-pixels reduced to ~0.0173 sec and ~0.0046 sec, respectively. Considering the fact that the frame rate of the RCM device used is ~9 frames per second (~0.111 see/image), this demonstrated virtual staining speed is sufficient for real-time operation in clinical settings.

DISCUSSION

Here, a deep neural network-based approach was applied to perform virtual staining in RCM images of label-free normal skin, BCC, and melanocytic nevi. Grayscale RCM images were also transformed into pseudo-H&E virtually stained images 40 that resembled H&E staining, the visualization format most commonly used by pathologists to assess biopsies of histochemically-stained tissue on microscopy slides.

Figure 15A:
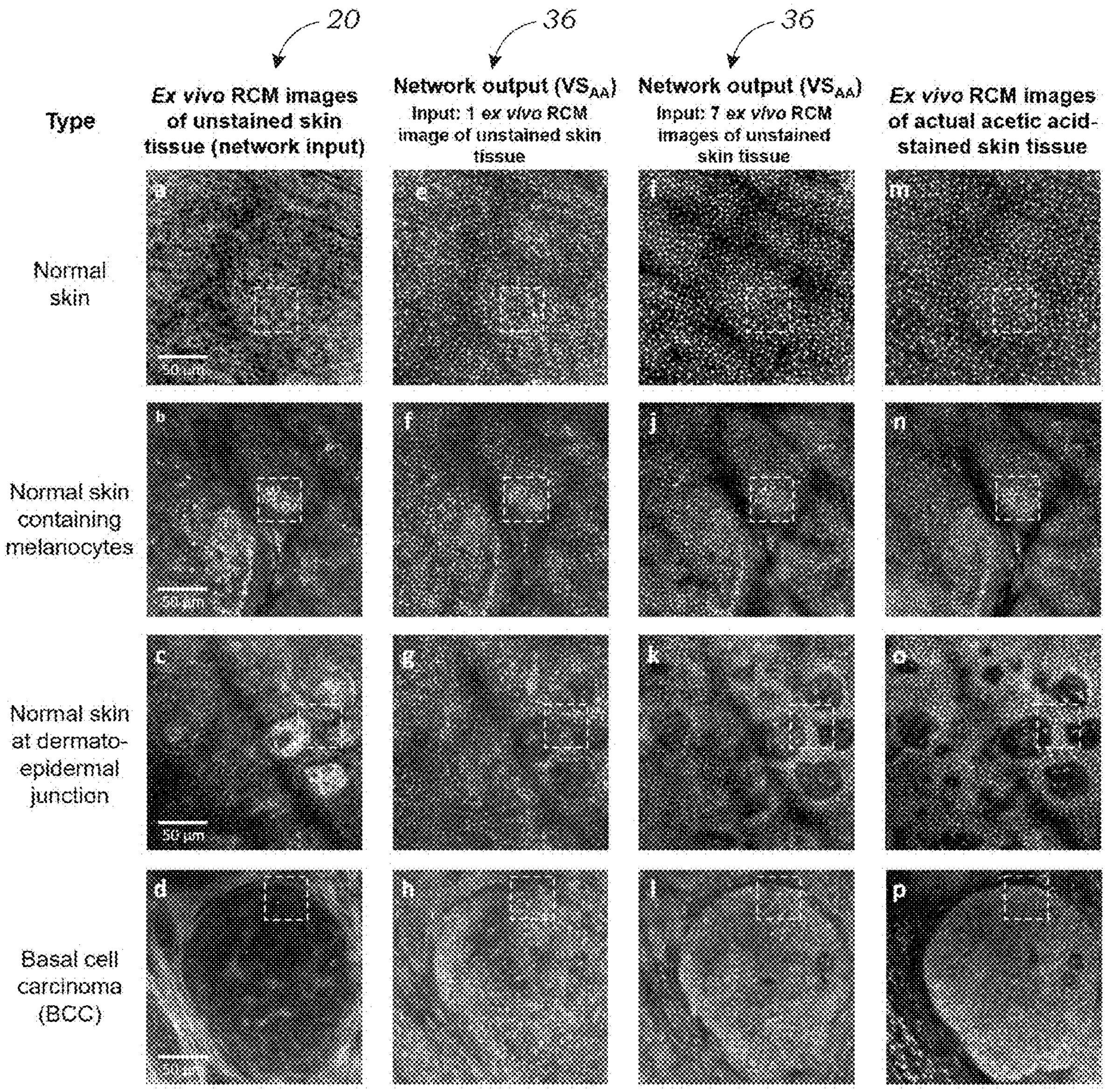
FIG. 15A. Comparison of the results obtained by the acetic acid virtual staining networks using 2D and 3D input. Image panels (a)-(d) are label-free RCM images of four different types of ex vivo skin tissue areas, including (a) normal skin, (b) normal skin containing melanocytes. (c) normal skin at dermal-epidermal junction and (d) skin containing BCC, which are used as network inputs. Image panels (e)-(h) are acetic acid virtual staining results of the same tissue areas in image panels (a)-(c), which are generated by a trained virtual staining network taking only one label-free RCM image as input. Image panels (i)-(l) are same as image panels (e)-(h) but the images are generated by a trained virtual staining network taking 7 label-free RCM images that are axially neighbored as input, m-p, Ex vivo RCM images of the same tissue area and depths as in image panels (a)-(d) after the actual acetic acid staining process, serving as the ground truth for image panels (e)-(h) and image panels (i)-(l).
Figure 15B:
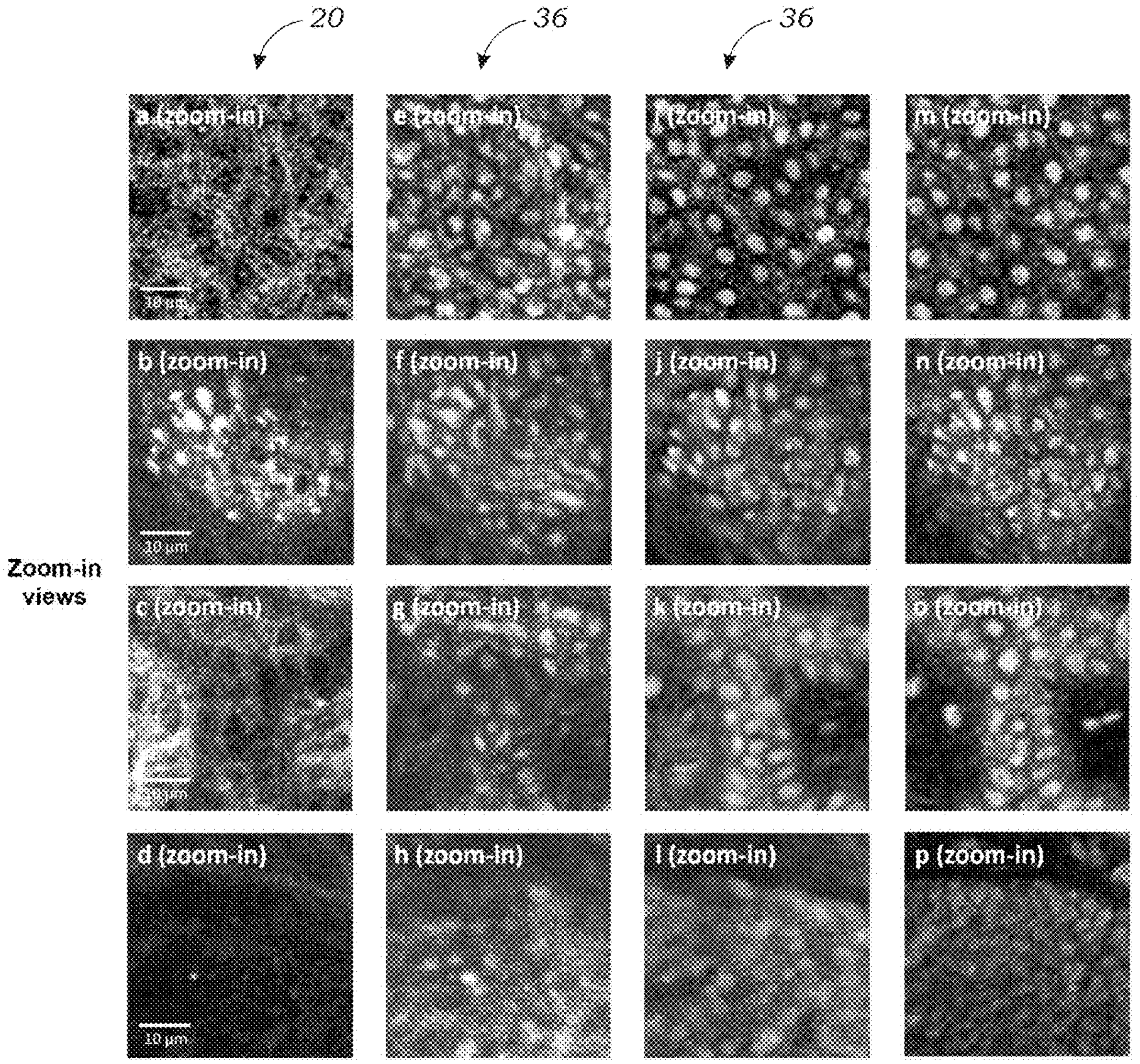
FIG. 15B shows zoomed-in images of dashed region in image panels (a)-(p) of FIG. 15A.

In the virtual staining inference, a 3D image stack (stack of images 20) was used as the input of the GAN model. An ablation study was conducted to demonstrate that using 3D RCM image stacks, composed of seven (7) adjacent images, is indeed necessary for preserving the quality of the acetic acid virtual staining results. For this comparative analysis, the input of the network $VS_{AA}$ 10 was changed to only one RCM image 20 of unstained skin tissue that was located at the same depth as the actual acetic acid-stained target (ground truth image). Then, a new $VS_{AA}$ 10 was trained without having a major change to its structure, except that the first three 3D convolutions were changed to 2D (see FIGS. 8A-8B for the original network structure). Compared to acetic acid virtual staining results that were obtained using 3D RCM image stacks as input, the results that used a single 2D RCM image 20 as input produced suboptimal results that were significantly blurred (see FIGS. 15A-15B image panels a-p). The reason for this degradation is that, compared to a single RCM image input 20, a 3D RCM image stack containing multiple adjacent slices or images 20 provides a more accurate basis for learning and virtual staining inference due to the additional input information provided by 3D spatial structure.

Using the presented virtual staining framework, good concordance was shown between virtual histology and common histologic features in the stratum *spinosum*, dermal-epidermal junction, and superficial dermis, areas of skin most commonly involved in pathological conditions. Virtually stained RCM images 40 of BCC show analogous histological features including nodules of basaloid cells with peripheral palisading, mucin, and retraction artifact. These same features are used to diagnose BCC from skin biopsies by pathologists using H&E histology. It was further demonstrated that the virtual staining network successfully inferred pigmented melanocytes in benign melanocytic nevi (see FIG. 14 image panels a-o).

While the results demonstrate success in obtaining histology quality images in vivo without the need for invasive biopsies, several limitations remain for future investigation and improvement. First, a limited volume of training data was used which was primarily composed of nodular BCC, which contained round nodules. When applied to another type of BCC from the blind testing set containing infiltrative, strand-like tumor islands of BCC with focal keratinization, it resulted in a form of artifact composed of dark blue/purple streaks of basaloid cells similar to the cords/strands seen in the microscopic image of frozen section histology from this sample, but with lower resolution (see FIG. 12 image panels a-d). Bias of the training set towards nodular BCC, may have hampered the generalization performance of the networks 10, 12. In order to address this issue, additional data on different types of BCC would be needed for training the networks 10, 12 to recognize differences in nuclear structure of BCC subtypes.

Another limitation of the virtual histology framework is that not all nuclei were placed with perfect fidelity in the transformed, virtually stained images 40. In the quantitative analysis for prediction of nuclei, there remained a positional misalignment between the network inputs and the corresponding ground truth images. This resulted in relatively imprecise learning of the image-to-image transformation for virtual staining, and therefore can be thought of as “weakly paired” supervision. To mitigate this misalignment error in the training image acquisition (time-lapsed RCM imaging process), one can reduce the number of RCM images 20 in a stack in order to decrease the time interval between successive RCM stacks. This may help capture more continuous 3D training image sequences to improve the initial registration of the ground truth images with respect to the input images. One can also further improve the learning-based image registration algorithm (see FIG. 7D) to be able to process volumetric spatial information in 3D RCM image stacks, helping to reduce axial misalignment errors due to e.g., sample deformation during the staining process, which can cause translation and tilting of the target image plane. Furthermore, distinct nuclei in virtually stained RCM images 40 of BCC tumor islands did not show exactly the same placement, size, and patterns as with ex vivo ground truth acetic acid staining and standard histology results (see FIGS. 4A, 4B image panels c, f, i, l, o—bottom row, FIG. 5 image panels a-p and FIG. 12). A likely reason for this may be the presence of mucin, which absorbs the penetrated light and reduces the reflectance of peripheral spatial features that can be used for the network inference. In addition, as light from the RCM penetrates deeper into tissue, image resolution decreases due to lower signal-to-noise (SNR).

All in all, the described virtual histology approach can allow diagnosticians to see the overall histological features, and obtain in vivo “gestalt diagnosis”, as pathologists do when they examine histology slides at low magnification. Ground truth histology was also collected from the same specimen used for RCM imaging (see FIG. 5 image panels j, k and FIGS. 9A-9B) and showed that virtual images 40 and ground truth histology images share similar features. Due to the series of complicated and destructive operations required for biopsy and H&E histochemical staining, one is naturally unable to compare identical regions of in vivo and ex vivo RCM processed H&E histology. Overall, the results show that the virtual staining networks 10, 12 can reconstruct BCC nodules and melanocytes within nevi appropriately with features and color contrast commonly seen in histologically stained microscopy sections. Further investigation is required to understand how virtual histology affects diagnostic accuracy, sensitivity and specificity when compared to grayscale contrast RCM images 20. Moreover, larger datasets and clinical studies are needed to further evaluate the clinical utility of the virtual histology algorithm. Specifically, studies should address whether it improves the diagnostic interpretation of skin conditions by expert RCM users, and reduces the amount of advanced training required for novice RCM users. The ability to switch between the original grayscale images 20 and pseudo-H&E virtual stained images 40 in real time may further improve diagnostic capabilities of in vivo RCM. Finally, if image stacks acquired at successive depths in the horizontal plane are reconstructed to produce virtually stained volumetric data, images 40 can also be examined in the vertical plane in a similar fashion to traditional skin histology.

Deep learning-enabled in vivo virtual histology is disclosed to transform RCM images 20 into virtually-stained images 40 for normal skin, BCC, and melanocytic nevi. Future studies will evaluate the utility of the approach across multiple types of skin neoplasms and other non-invasive imaging modalities towards the goal of optical biopsy enhancement for non-invasive skin diagnosis.

Methods

In Vivo RCM Image Acquisition

Following informed consent (Advarra IRB, Pro00037282), 43 patients had RCM images 20 captured during regularly scheduled visits. RCM images 20 were captured with the VivaScope 1500 System (Caliber I.D., Rochester, NY), by a board-certified dermatologist trained in RCM imaging and analysis. RCM imaging was performed through an objective lens-to-skin contact device that consists of a disposable optically clear window. Of course, the systems and methods herein are not limited to a particular make or model of microscope (e.g., portable RCM microscopes or imagers 110 may also be used). The window was applied to the skin over a drop of mineral oil and used throughout the imaging procedure. The adhesive window was attached to the skin with a medical grade adhesive (3M Inc., St. Paul, MN). Ultrasound gel (Aquasonic 100, Parker Laboratories, Inc.) was used as an immersion fluid, between the window and the objective lens. Approximately three RCM mosaic scans and two z-stacks were captured stepwise at 1.52 μm or 4.56 μm increments of both normal skin and skin lesions suspicious for BCC. Upon completion of RCM imaging, patients were managed as per standard-of-care practices. In several cases, skin lesions that were imaged in vivo were subsequently biopsied or excised using standard techniques and the excised tissue was subjected to ex vivo RCM imaging and/or diagnostic tissue biopsy. Tissue diagnosis was confirmed by a board-certified dermatopathologist.

The final in vivo blind testing dataset that was used to present the in vivo results reported in this paper was composed of 979 896×896 RCM images 20 collected in vivo without any acetic acid-stained ground truth. Histopathologic confirmation was obtained on all skin lesions/tumors but was not provided on in vivo RCM images of normal skin.

Skin Tissue Sample Preparation for Ex Vivo RCM Imaging

Discarded skin tissue specimens 50 from Mohs surgery tissue blocks with and without residual BCC tumor were retrieved for ex vivo RCM imaging with IRB exemption determination (Quorum/Advarra, QR #: 33993). Frozen blocks were thawed, and the specimens were thoroughly rinsed in normal saline. Small samples of intact skin stratum corneum, epidermis, and superficial dermis were trimmed from tissue specimens. The skin sample length and width varied depending on the size of the discarded Mohs specimen. The adipose and subcutaneous tissue was trimmed from the superficial skin layers, such that skin samples from stratum corneum to the superficial dermis were approximately 2 mm thick. The trimmed skin samples 50 were placed flat onto an optically clear polycarbonate imaging window with the stratum corneum side down and placed in a tissue block made from 4% agarose (Agarose LE, Benchmark Scientific). The agarose solution was brought to a boiling point and approximately 0.1 mL-0.3 mL was pipetted over the trimmed skin sample and imaging window until that the entire sample was covered by the agarose solution. 10 min was given for the agarose solution to cool to room temperature, hardening into a malleable mold that encapsulated the skin tissue sample flat against the imaging window. A 2 mm curette was used to channel a small opening in the agarose mold to access the center of the skin tissue sample while the perimeter of the sample remained embedded in the agarose mold.

Ex Vivo RCM Image Acquisition of Tissue Blocks

The imaging window with the agarose molded skin tissue 50 was attached to the RCM device (VivaScope 1500, Caliber I.D., Rochester. NY), which operates at a frame rate of 9 frames/sec. Ultrasound gel (Aquasonic 100, Parker Laboratories, Inc.) was used as an immersion fluid, between the window and the objective lens. The optical head of the RCM device was inverted. Image z-stacks containing 40 images each were captured stepwise with 1.52 μm increments to a total depth of 60.8 μm. 10-20 consecutive image stacks were captured in a continuous time-lapse fashion over the same tissue area. Areas with features of interest (e.g., epidermis, dermal-epidermal junction, and superficial dermis, etc.) were selected before imaging. The first image stack captured RCM images 20 of label free skin tissue. After completion of the first image stack, 1-2 drops of 50% acetic acid solution (Fisher Scientific) were added to small opening in the agarose mold with access to the center of the skin tissue sample. While 5% acetic acid is sufficient to stain nuclei of normal skin tissue, a higher concentration was required to penetrate mucin that often surrounds islands of BCC tumor, and thus a standard 50% solution was added to all tissue. RCM time-lapse imaging continued until acetic acid penetrated the area of interest and stained cell nuclei throughout the depth of the image stack. Before and after time-lapse imaging, RCM mosaics (Vivablocks) of the skin tissue sample were also captured at one or several depths. After ex vivo RCM imaging, samples were either fixed in 10% neutral buffered formalin (Thermo Fisher Scientific, Waltham, MA) for histopathology or safely discarded.

The final ex vivo training, validation and testing datasets that were used to train the deep networks 10, 12 and perform quantitative analysis of its blind inference results were composed of 1185, 137 and 199 896×896-pixel ex vivo RCM images of unstained skin lesions and their corresponding acetic acid-stained ground truth, which were obtained from 26, 4 and 6 patients, respectively.

Image Preprocessing and Registration

Accurate alignment of the training image pairs is of critical importance for the virtual staining deep neural networks 10, 12 to learn the correct structural feature mapping from the unstained tissue images to their stained counterparts. The principle of the image registration method relies on the spatial and temporal consistency of the time-lapse volumetric image stack captured using RCM during the staining process of the ex vivo tissue samples. In other words, the raw data cover essentially 4-dimensional space, where the three dimensions represent the volumetric images of the tissue and the fourth dimension (time) records the whole staining process of the tissue, i.e., from the unstained state to the stained state, as a function of time.

FIG. 7A provides an overview of the image registration workflow. The first part of the registration process starts with performing an "initial registration" (operation 200) to achieve coarsely registered image pairs, which includes two sub-steps as depicted in FIG. 1B. In sub-step (1) of the initial registration 200, a certain depth of the time-lapse volumetric image stack at hand was manually selected, and iteratively applied a pyramid elastic registration algorithm to each of the image pairs that are at this depth, but captured at successive time points. For this, an image sequence was used where all the images are located at the same depth and aligned throughout the staining process. In sub-step (2) of the initial registration 200, the images were manually inspected in this aligned image sequence and picked two images that have 0% and 100% nuclei stained, i.e., referring to "before staining" and "after staining" phases, respectively. The corresponding z-stacks that these two picked images belong to were found and performed a stack registration based on the same elastic registration algorithm used in sub-step (1). As a result of this initial registration process 200, all the images 20 in these two stacks were roughly aligned with each other, by and large eliminating the large-scale elastic deformations that occurred during the imaging and staining process, forming the initially-registered input-target image pairs.

At this stage, it is noteworthy that small shifts and distortions between the two sets of initially-registered images can still exist and lead to errors during the learning process. To mitigate this, these image pairs were further aligned at a sub-pixel level through the second part of the registration process. In this part, the coarsely registered image pairs were individually fed into a convolutional neural network A (operation 210), whose structure is similar to the generator network reported in FIGS. 8A-8B except that the number of channels and downsampling operations are fewer, and the first few 3D convolutions are replaced with 2D convolutions (see the "Network architecture and training schedule" sub-section in Methods for details). Then, a soft training of network A using all these images is utilized to transform the input images to visually resemble the sought target. The aim of this method is to build an initial bridge between the input and target images to facilitate their accurate alignment. Using the pyramid elastic registration method, the target images were aligned against the output of the network A, thus achieving more accurate spatial correspondence between the unstained input and the corresponding target images; this step is termed as the "$1^{st}$ fine registration" as seen in operation 220 of FIG. 7A. Note that all the elastic registration algorithms mentioned till now perform spatial transformation based on a displacement vector field (DVF) of the image pair, which is calculated through the multi-scale correlation between the two images that form a pair (see FIG. 7C).

Despite its utility, the calculation of multi-scale correlation can frequently produce abnormal values on DVFs, which result in unsmooth distortions in the registered images from time to time. To mitigate this problem, another round of soft training (operation 230) was applied of a separate network A'(that is similar to A) and a second fine registration step (operation 240) to further improve the registration accuracy. Unlike the $1^{st}$ fine registration, this $2^{nd}$ fine registration step (operation 240) was performed based on the DVF generated by a learning-based algorithm, where a deep convolutional neural network B is trained to learn the smooth, accurate DVF between two input images. The training details of this network B are reported in FIG. 7D. In the training phase, the network B is fed with the cropped patches of the output of network A', i.e., $I_f$, along with the roughly registered target image patches, $I_m$, and generates a predicted DVF $\phi$ that indicates the pixelwise transformation from $I_m$ to $I_f$, such that $I_m$ serves as "moving" patches and $I_f$ serves as "fixed" patches. Then, $I_m$ is spatially deformed using $\phi$ so that the predicted registered target patches, $I_r$, are produced. To create the data with smooth and accurate spatial transformations, serving as ground truth for training B, the previous pyramid elastic registration (based on multi-scale correlation) was performed once again using only ~10% of the roughly registered image pairs (i.e., output images of A' and their roughly registered targets). During this process, the pyramid elastic registration algorithm was fine-tuned to obtain optimal spatial transformations so that the target patches $I_{r,gt}$ and the corresponding DVFs $\phi_{gt}$ can be accurately registered. Using these $I_{r,gt}$ and $\phi_{gt}$ with their corresponding $I_m$ and $I_f$, a training set was formed and the supervised training of the network B was performed, where the loss function was selected to minimize the difference of both $(I_r - I_{r,gt})$ and $(\phi - \phi_{gt})$ using mean square error loss, and the total variation (TV) of $\phi$. Once the network B was successfully trained and used to perform inference across the entire image dataset, the target images were much more accurately aligned with the output of network A', eliminating various registration artifacts. Finally, through this approach one generates the registered acetic acid-stained target images that are aligned accurately against the unstained/label-free input RCM images, making it ready for training the acetic acid virtual staining network ($VS_{AA}$) 10, which is detailed below.

Generative Model and Loss Functions

A pix2pix GAN framework was used as the generative model of acetic acid virtual staining network ($VS_{AA}$) 10, which includes the training of (1) a generator network for learning the statistical transformation between the unstained input stacks of RCM images 20 and the corresponding acetic acid stained tissue images, and (2) a discriminator network for learning how to discriminate between a true RCM image of an actual acetic acid-stained skin tissue and the generator network's output, i.e., the corresponding virtually stained (acetic acid) tissue image 36. The merit of using this pix2pix GAN framework stems from two aspects. First, it retains the structural distance penalty in a regular deep convolutional network, so that the predicted virtually stained tissue images can converge to be similar with their corresponding ground truth in overall structural features. Second, as a GAN framework, it introduces the competence mechanism by training the two aforementioned networks in parallel. Due to the continuous enhancement of the discrimination ability of the discriminator network during the training process, the generator must also continuously generate more realistic images to deceive the discriminator, which gradually impels the feature distribution of the high-frequency details of the generated images to conform to the target image domain. Ultimately, the desired result of this training process is a generator, which transforms an unstained input RCM image 20 stack into an acetic acid virtually stained tissue image 36 that is indistinguishable from the actual acetic acid-stained RCM image of the same sample at the corresponding depth within the tissue. To achieve this, following the GAN scheme introduced above, the loss functions of the generator and discriminator networks were devised as follows:

$$\mathcal{L}_{generator} = \mathcal{L}_{structral}\{I_{target}, G(I_{input\_stack})\} + \alpha \times TV\{G(I_{input\_stack})\} + \lambda \times (1 - D(G(I_{input\_stack})))^2, \quad (1)$$

$$\mathcal{L}_{discriminator} = D(G(I_{input\_stack}))^2 + (1 - D(I_{target}))^2, \quad (2)$$

where G(•) represents the output of the generator network, D(•) represents the output probabilistic score of the discriminator network, $I_{target}$ denotes the image of the actual acetic acid-stained tissue used as ground truth, $I_{input\_stack}$ denotes the input RCM image stack (unstained). The generator loss function Eq. (1) aims to balance the pixel-wise structural error of the generator network output image with respect to its ground truth target, the total variation (TV) of the output image, and the discriminator network's prediction of the generator network's output, using the regularization coefficients ($\alpha$, $\lambda$) that are empirically set as (0.02, 15). Specifically, the structural error term $\mathcal{L}_{structural}$ takes a form of the reversed Huber (or "BerHu") error, which blends the traditional mean squared error and mean absolute error using a certain threshold as the boundary. The reversed Huber error between 2D images a and b is defined as:

$$\mathcal{L}_{BerHu}\{a, b\} = \sum_{\substack{m,n \\ |a(m,n)-b(m,n)|\le\delta}} |a(m, n) - b(m, n)| + \sum_{\substack{m,n \\ |a(m,n)-b(m,n)|>\delta}} \frac{|a(m, n) - b(m, n)|^2 + \delta^2}{2\delta}, \tag{3}$$

where m, n are the coordinates on the images, and $\delta$ is a threshold hyperparameter that is empirically set as 20% of the standard deviation of the normalized ground truth image $z_{target}$. The third term of Eq. (1) penalizes the generator to produce outputs that are more realistic to the discriminator by maximizing the discriminator's response to be 1 (real, like an actual acetic acid-stained tissue image), which increase authenticity of the generated images. The discriminator loss function Eq. (2) attempts to achieve the correct classification between the network's output and its ground truth by minimizing the score of the generated image to be 0 (classified to be a virtually stained tissue image) and maximizing the score of the actual acetic acid-stained tissue image to be 1 (real, classified to be actual/real acetic acid-stained tissue image). Within this adversarial learning scheme, spectral normalization was applied in the implementation of the discriminator network to improve its training stability.

Network Architecture and Training Schedule

For the generator network, as shown in FIG. 8A, an attention U-Net structure (encoder—decoder with skip connections and attention gates) was employed to learn the 3D transformation from the label-free unstained RCM image 20 stack to the acetic acid virtually stained tissue image 36, which was adapted to work on 3D input distributions, matching the input RCM image stacks. For each sample, a stack of seven (7) RCM images 20 (unstained) adjacent in depth and with an axial step size of 1.52 μm are used as the network 10 input and encoded in the depth dimension of the network, and the U-Net generates a single virtually stained tissue image 36 that is corresponding to the central plane of the image stack. In other words, the output image is at the same level as the $4^{th}$ image in the input stack. In the U-Net structure, there is a downsampling path and a symmetric upsampling path. In the downsampling path, there are five convolution—downsampling blocks, each consisting of 1) three 3×3 successive 2D convolutional layers with batch normalization layers and leaky rectified linear unit (leaky ReLU, with a slope of 0.2) in between to extract and encode spatial features, and 2) one 2×2 2D average pooling layer with a stride of 2×2 to perform a 2× downsampling. Note that rather than using 2D convolution, the first block uses three 3D convolutional layers with a kernel size of 3×3×3 and without padding in the depth dimension, which shrinks (after three layers) the depth size of the input tensor from 7 to 1, resulting in 2D outputs that are consistent with the following convolutional operations of the U-Net structure. Also, there is a residual connection communicating the first and last tensor in each block with an addition operation. Following the downsampling path, the upsampling path has five corresponding convolution—upsampling blocks. The input of each block is a channel dimension concatenation of the output tensor of previous block in the upsampling path and the attention gated output tensor at the corresponding level in the downsampling path, which create skip connections between the upsampling path and downsampling path. It is worth noting that to alleviate irrelevant spatial information propagated in the simple skip connection of the U-Net, soft attention gate blocks were also employed in each skip connection, including a few convolutional layers and a sigmoid operation to calculate the activation weight maps, such that the feature maps from the downsampling encoder path are pixel-wise multiplicatively weighted and propagated to the upsampling decoder path. The structure of the upsampling block is quite similar to the downsampling path, except that (1) the pooling layers are replaced by 2× bilinear upsampling layers and (2) there is no residual connection.

As depicted in FIG. 8B, the discriminator is a convolutional neural network that consists of five successive convolutional blocks. Each block is composed of one 3×3 2D convolutional layer with a stride of 1×1, one 2×2 2D convolutional layer with stride of 2×2 to perform 2× downsampling and leaky ReLU layers after each convolutional layer. After the last convolutional block, an average pooling layer flattens the output tensor to 1×1 but keeps the channel dimension, subsequently fed into a two-layer fully connected block of size 1024×1024 and 1024×1. The final output represents the discriminator probabilistic score, which falls within (0, 1), where 0 represents a false and 1 represents a true label.

Figure 16A:
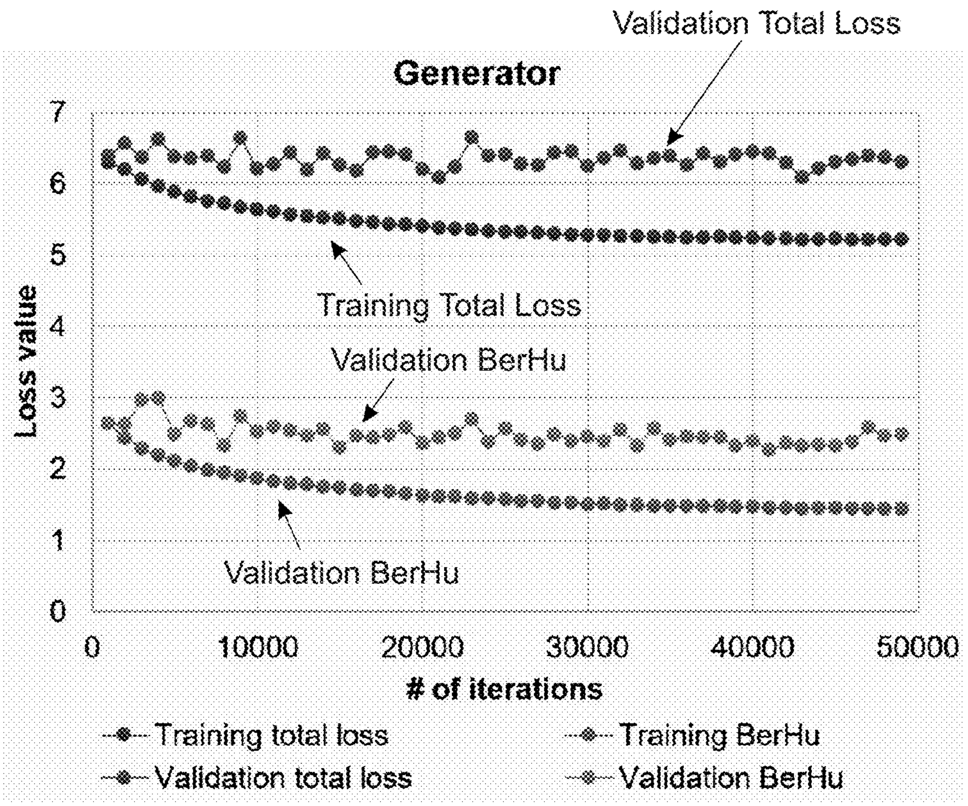
FIGS. 16A-16B: Loss curves during the training of the virtual staining neural network.
Figure 16B:
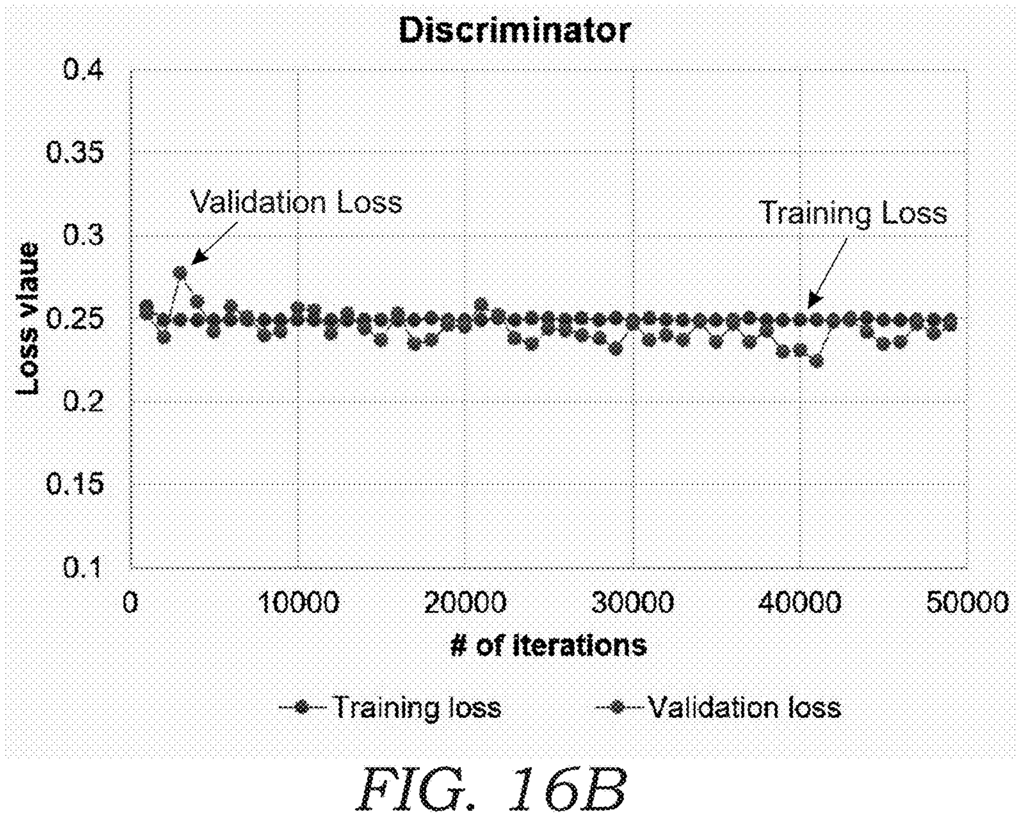

During the training of this GAN framework, the input image stacks and the registered target images were randomly cropped to patch sizes of 256×256×7 and 256×256, respectively and used a batch size of 12. Before feeding the input images data augmentation was also applied, including random image rotation, flipping and mild elastic deformations. The learnable parameters were updated through the training stage of the deep network using an Adam optimizer with a learning rate of $1\times10^{-4}$ for the generator network and $1\times10^{-5}$ for the discriminator network. Also, at the beginning of the training, for each iteration of the discriminator, there are 12 iterations of the generator network, to avoid the mode collapse, following a potential overfitting of the discriminator network to the targets. As the training evolves, the number of iterations ($t_{GperD}$) of the generator network for each iteration of the discriminator network linearly decreases, which is given by $$t_{GperD} = \max\left(3, \left\lfloor 12 - 0.25\left\lfloor \frac{t_D}{1000} \right\rfloor \right\rfloor\right), \tag{4}$$

where $t_D$ denotes the total number of iterations of the discriminator, $\lfloor\bullet\rfloor$ represents the ceiling functions. Usually, the $t_D$ is expected to be ~40000 iterations when the generator network converges. A typical plot of the loss functions during the GAN training is shown in FIGS. 16A-16B.

H&E Virtual Staining

For the pseudo-H&E virtual staining of the actual and virtual acetic acid-stained tissue images, an earlier approach was modified, where epi-fluorescence images were used to synthesize pseudo-color images with H&E contrast. The principle of the pseudo-H&E virtual staining relies on the characteristics of H&E staining that the nucleus and cytoplasm are stained with blue and pink, respectively. In this system and method, an unstained input image collected by RCM ($I_{input}$) and its corresponding actual acetic acid-stained tissue image ($I_{target}$) are subtracted in pixel intensities to extract the foreground component $I_{foreground}$ that mainly contains the nuclear features:

$$I_{foreground,target}=\max(1.2\times I_{target}-0.8\times I_{input},\,0). \tag{5}$$

Note that $I_{target}$ and $I_{input}$ are initially normalized to (0, 1), and all the operations in Eq. (5) are pixel-wise performed on the 2D images. The selection of the coefficients 1.2 and 0.8 here is empirical. The background component that contains other spatial features including cytoplasm is defined by simply using the unstained input images $I_{input}$. Following this separation of the foreground and background components, a pseudo-H&E acetic acid-stained tissue image $I_{analytical\text{-}HE,target}$ is analytically computed by colorizing and blending these two components based on a rendering approach, which models transillumination absorption using the Beer-Lambert law:

$$I_{analytical-HE,target}=\exp(-\beta_{hematoxylin}I_{foreground,target})\exp(-\beta_{eosin}I_{input}), \tag{6}$$

where $\beta_{hematoxynlin}$ and $\beta_{eosin}$ are the 3-element weight vector corresponding to R, G and B channels that helps to mimic the real color of hematoxylin and eosin, respectively. In the experiments disclosed herein, the values of the elements in $\beta_{hematoxylin}$ and $\beta_{eosin}$ are empirically chosen as $[0.84, 1.2, 0.36]^T$ and $[0.2, 2, 0.8]^T$, respectively. Similarly, a pseudo-H&E acetic acid virtually stained tissue image $I_{analytical\text{-}HE,output}$ can also be computed by replacing $I_{target}$ with an acetic acid virtually stained tissue image $I_{output}$ in Eq. (5).

Figure 18A:
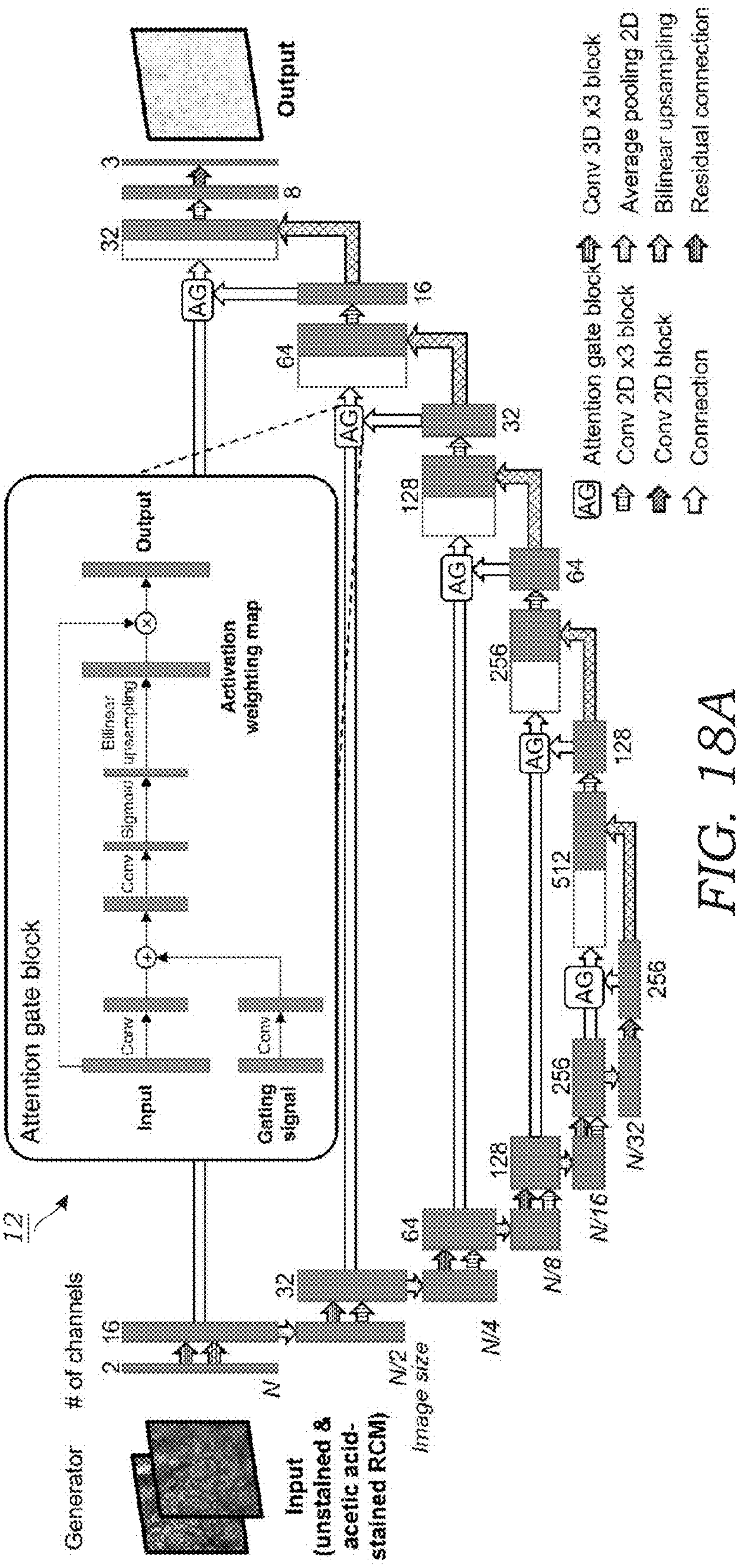
FIGS. 18A-18B illustrate the architecture of the GAN-based deep neural network used for generating pseudo-H&E stained images.
Figure 18B:
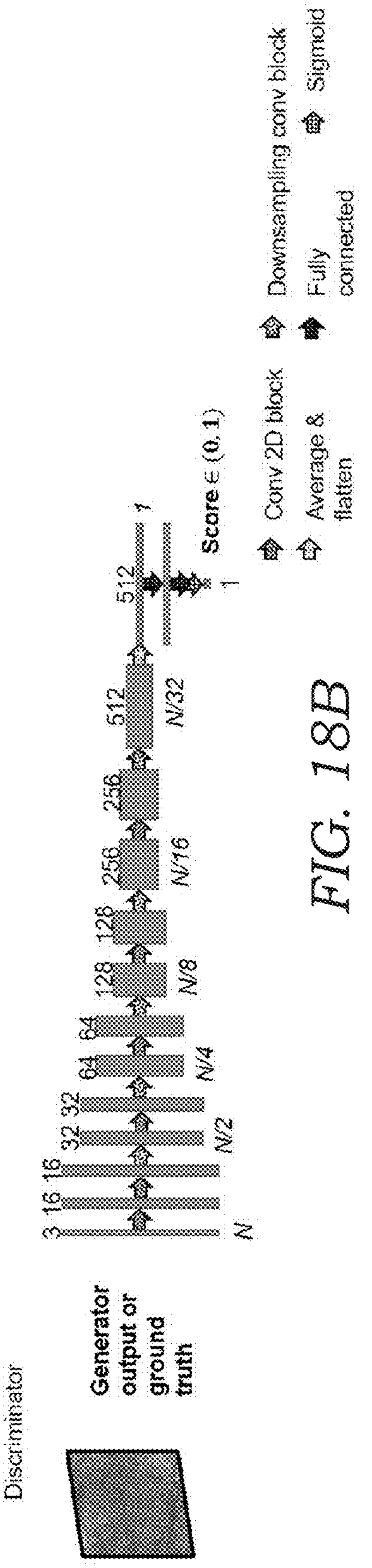

This analytical approach (Eq. 6) works well on most of the actual and virtual acetic acid-stained tissue images to create H&E color contrast. However, when it comes to the images that contain melanocytes, whose H&E stain produces dark brown, this algorithm fails to generate the correct color at the position of these melanocytes. Considering that the brown color (representing melanin) would not be possible to generate through a pixel-wise linear combination of the images $I_{input}$ and $I_{target}$ or $I_{output}$, a learning-based approach was introduced to perform the correct pseudo-H&E virtual staining ($VS_{HE}$), which can incorporate inpainting of the missing brown features by using the spatial information content of the images. For training purposes, manual labeling of melanocytes was performed to create training data for this learning-based approach. In order to reduce the labor of this manual labeling, first the initial distribution of melanin in a certain field of view was estimated through an empirical formula:

$$I_{melanin}=\begin{cases} I_{input}, & \text{where } I_{target}\cdot I_{input}>I_{th} \\ 0, & \text{otherwise} \end{cases}, \tag{7}$$

where • denotes pixel-wise multiplication, and $I_{th}$ represents a threshold that is selected as 0.2 based on empirical evidence. The constitution of this formula is based on the observation that melanin has strong reflectance in both the unstained/labelfree and actual acetic acid-stained tissue RCM images, namely $I_{input}$ and $I_{target}$, respectively. Then, these initial estimations are further cleaned up through a manual labeling process performed with the assistance of a board-certified dermatopathologist, resulting in $I_{melanin,labeled}$. This manual labeling process as part of the training forms the core task that will be learned and executed by the learning-based scheme (FIGS. 18A-18B). Similar to Eq. (6) but with one more term added, the corrected pseudo-H&E virtual staining results for the actual acetic acid-stained tissue images $\tilde{I}_{analytical\text{-}HE,target}$ can be computed as:

$$\tilde{I}_{analytical-HE,target}=\exp(-\beta_{hematoxylin}I_{foreground,target})\exp(-\beta_{eosin}I_{input})\exp(-\beta_{brown}I_{melanin,labeled}), \tag{8}$$

where the value of $\beta_{brown}$ is empirically chosen as $[0.12, 0.24, 0.28]^T$ in order to correctly render the brown color of the melanin. Using Eq. (8), the ground truth images were obtained for the learning-based virtual staining approach to perform the corrected pseudo-H&E virtual staining. Using the ex vivo training set, the pseudo-H&E virtual staining network $VS_{HE}$ 12 was trained to transform the distribution of the input and actual acetic acid-stained tissue images, i.e., $I_{input}$ and $I_{target}$, into $I_{analytical\text{-}HE,target}$. The architecture of the network $VS_{HE}$ 12 is identical to the ones used in the registration process, except for that the input and output of the network $VS_{HE}$ 12 have 2 and 3 channels, respectively (FIGS. 18A-18B). Once the training is finished, the resulting network $VS_{HE}$ 12 was used to perform pseudo-H&E virtual staining of the previously generated acetic acid virtually stained tissue images $I_{output}$ in the testing set. The network $VS_{HE}$ 12 took $I_{output}$ along with input images $I_{input}$ to generate pseudo-H&E virtually stained tissue images $\tilde{I}_{VS\text{-}HE,output}$ with the correct color for melanin:

$$\tilde{I}_{VS-HE,output}=VS_{HE}(I_{output},\,I_{input}). \tag{9}$$

Figure 17:
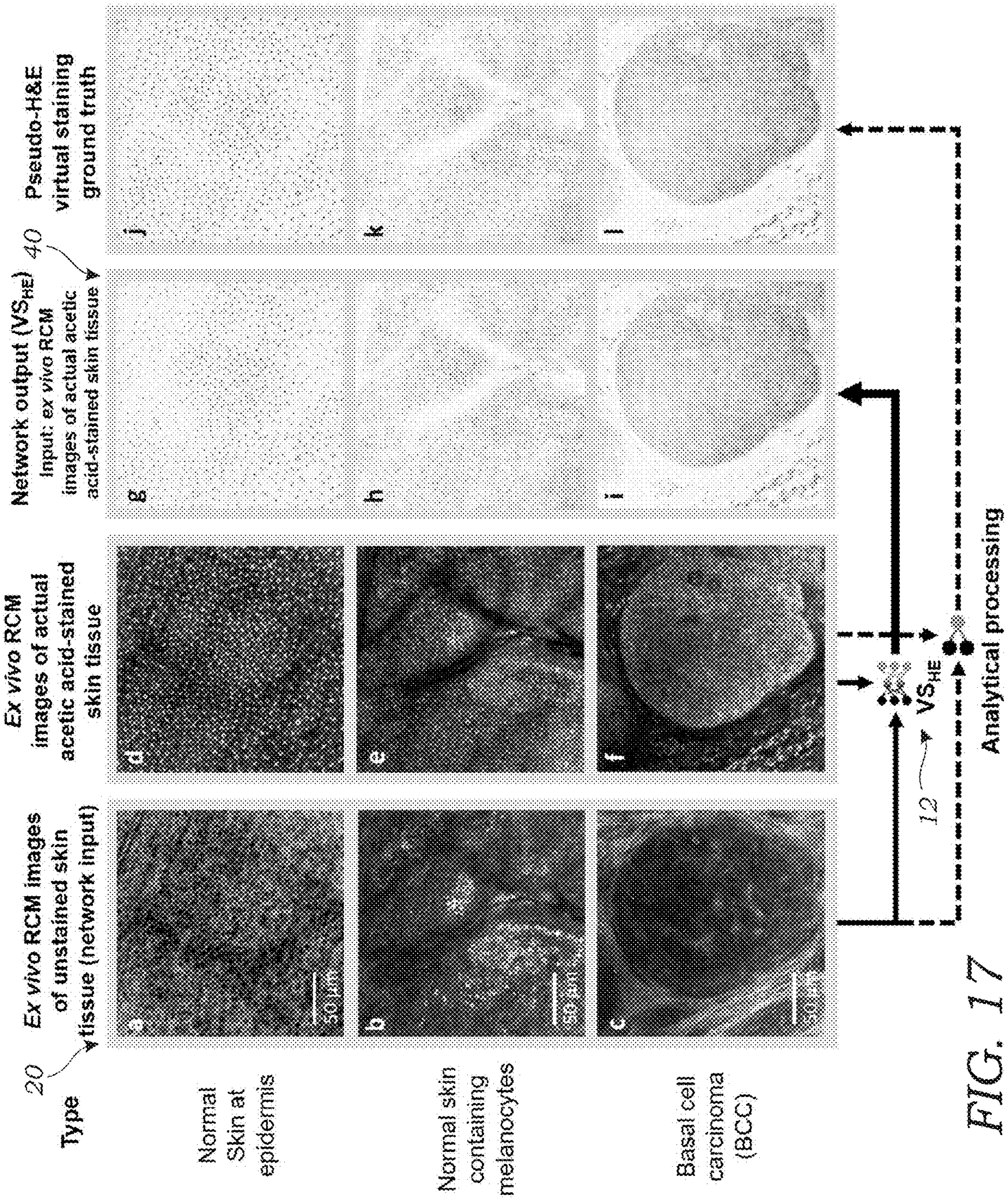
FIG. 17 illustrates a comparison of the pseudo-H&E virtual staining results against their ground truth generated by analytical processing. Image Panels (a)-(c) are label-free RCM images of three different types of ex vivo skin tissue areas, including (a) normal skin, (b) a melanocytic nevus and (c) skin containing BCC, which are used as input of the virtual staining neural networks. Image panels (d)-(f) are, RCM images of the same tissue area and depth as (a)-(c) after the actual acetic acid staining process. Image panels (g)-(i) are pseudo-H&E virtual staining results generated using the actual acetic acid-stained images of image panels (d)-(f). These H&E images were generated by the same virtual staining network $VS_{HE}$ that took the RCM images of the unstained tissue of image panels (a)-(c) and actual acetic acid-stained images of image panels (d)-(f) as input (see solid arrows). Image panels (j)-(l) are pseudo-H&E ground truth images for image panels (g)-(i), which were generated by analytical processing (using Eq. (8) in Methods section).

Eq. (9) was used to create all the pseudo-H&E virtually stained tissue images. To exemplify the effectiveness of this learning-based pseudo-H&E virtual staining approach, in FIG. 17 (image panels a-l) a comparison is shown between the pseudo-H&E virtual staining results against their counterparts generated by Eq. (8) using a few examples on the testing test, which demonstrates a decent correspondence between the two approaches.

Quantitative Morphological Analysis of Virtual Staining Results

CellProfiler was used to conduct morphological analysis of the results. After loading the actual acetic acid-stained tissue images and virtually stained (acetic acid) tissue images using CellProfiler, cell segmentation and profile measurement were performed to quantitatively evaluate the quality of the predicted images when compared with the corresponding ground truth images. In CellProfiler, the typical diameter of objects to detect (i.e., nuclei) was set to 10-25 pixel units and objects that were outside the diameter range or touching the border of each image were discarded. An adaptive thresholding strategy was applied using minimum cross-entropy with a smoothing scale of 6 and a correction factor of 1.05. The size of the adaptive window was set to 50. "Shape" and "Propagate" methods were selected to distinguish the clumped objects and draw dividing lines between clumped objects, respectively. Following this step, the function module "IdentifyPrimaryObjects" was introduced to segment the nuclei in a slice-by-slice manner. Accordingly, well-segmented nuclei images were obtained containing positional and morphological information associated with each detected nuclear object.

For the analysis of nuclear prediction performance of the model, first the function module "ExpandOrShrinkObjects" was employed to slightly expand the detected nuclei by e.g., 4 pixels (~2 μm), so that the image registration and nuclei tracking-related issues across different sets of images can be mitigated. Then the function module "RelateObjects" was used to assign a relationship between the objects of virtually stained nuclei and actual acetic acid-stained ground truth, and used "FilterObjects" to only retain the virtually stained nuclei objects that present overlap with their acetic acid-stained ground truth, which were marked as true positives (TP). Similarly, false positives (FP) and false negatives (FN) were marked based on the virtually stained nuclei objects that have no overlapping with their ground truth, and the actual acetic acid-stained nuclei objects that have no overlap with the corresponding virtually stained nuclei objects, respectively. Note that in this case one does not have true negative (TN) calculated since one cannot define a nuclear object that does not exist in both the virtually-stained and ground truth images. Next, the numbers of TP, FP and FN events were counted, which were denoted as $n_{TP}$, $n_{FP}$ and $n_{FN}$, respectively, and accordingly computed the Sensitivity and Precision values, defined as:

$$\text{Sensitivity} = \frac{n_{TP}}{n_{TP} + n_{FN}}, \tag{10}$$

$$\text{Precision} = \frac{n_{TP}}{n_{TP} + n_{FP}}. \tag{11}$$

For the nuclear morphological analysis, the function module "MeasureObjectSizeShape" was utilized to compute the nuclei area ("AreaShape_Area", the number of pixels in one nucleus), compactness ("AreaShape_Compactness", the mean squared distance of the nucleus's pixels from the centroid divided by the area of the nucleus), and eccentricity ("AreaShape_Eccentricity", the ratio of the distance between the foci of the effective ellipse that has the same second-moments as the segmented region and its major axis length). "MeasureObjectIntensity" module was employed afterward to compute the nuclei reflectance ("Intensity_IntegratedIntensity_Cell", the sum of the pixel intensities within a nucleus). The function module "MeasureTexture" was utilized to compute the contrast of the field of view ("Texture_Contrast_Cell", a measure of local variation in an image). For image similarity analysis, the Pearson Correlation Coefficient (PCC) was calculated for each image pair of the virtual histology results and the corresponding ground truth image based on the following formula:

$$PCC = \frac{\sum (I_{output} - E(I_{output}))(I_{target} - E(I_{target}))}{\sqrt{\sum (I_{output} - E(I_{output}))^2}\sqrt{\sum (I_{target} - E(I_{target}))^2}}, \tag{12}$$

where $I_{output}$ and $I_{target}$ represent the predicted (virtually-stained) and ground truth images, respectively, and E(•) denotes the mean value calculation. For all the violin plots presented above, the violin plot function in the Seaborn Python library was used to visualize the conformance between the prediction and ground truth images.

Network Implementation Details

The deep neural networks 10, 12 used herein were implemented and trained using Python (v3.6.5) and TensorFlow (v1.15.0. Google Inc.). All the image registration algorithms are implemented with MATLAB r2019a. For the training of the models, a desktop computer was used with dual GTX 1080 Ti graphical processing unit (GPU, Nvidia Inc.) and Intel® Core™ i7-8700 central processing unit (CPU, Intel Inc.) and 64 GB of RAM, running Windows 10 operating system (Microsoft Inc.). The typical training time of the convolutional neural networks used in the registration process and the pseudo-H&E virtual staining network (i.e., networks A, A', B, and $VS_{HE}$ 12) is ~24 hours when using a single GPU. For the acetic acid virtual staining network (i.e., $VS_{AA}$ 10), the typical training time for using a single GPU is ~72 hours. Once the $VS_{AA}$ and $VS_{HE}$ networks 10, 12 are trained, using the same computer with two GTX 1080 Ti GPUs one can execute the model inference at a speed of ~0.2632 sec and ~0.0818 sec for an image size of 896-896-pixels, respectively. Using a more powerful machine with eight Tesla A100 GPUs, the virtual staining speed can be substantially increased to ~0.0173 and ~0.0046 sec per image (896×896-pixels), for $VS_{AA}$ and $VS_{HE}$ networks, respectively.

Pyramid Elastic Registration Algorithm

The specific procedures of the pyramid elastic registration algorithm are detailed in the following pseudo-code set forth in Table 1:

TABLE 1

| Algorithm Pyramid elastic registration |
|---|
| Set the block size shrinking speed α, the minimum block size β, the shift error tolerance ε; |
| Initialize the number of blocks N using $N_0$; |
| Input the image pair $I_A$ and $I_B$ to be cross-registered; |
| Repeat: |
|   Divide both $I_A$ and $I_B$ into N × N image blocks; |
|   Repeat: |
|     Calculate the 2D cross-correlation map CCM between the corresponding blocks in $I_A$ and $I_B$; |
|     Calculate the shift amount of each pair of blocks through fitting a 2D Gaussian function to the peak of the CCM (see details below), forming a 2D shift map SM composed of N × N elements; |
|     Perform linear interpolation of SM to fit the image size of $I_A$ ($I_B$), producing SM'; |
|     Register $I_B$ to $I_A$ based on SM', creating a new $I_B$; |
|   Until the maximum value of the SM is smaller than the shift error tolerance ε; |
|   N ← round(N × α); |
| Until the block size is smaller than β; |
| Result: $I_B$ is finely registered to $I_A$ with sub-pixel level accuracy. |

For performing this elastic registration, the values of α, β, ε and $N_0$ are empirically set as 1.4, 50, 0.5 and 3, respectively. The detailed procedures of calculating the 2D shift map SM based on the 2D cross-correlation map CCM can be summarized as:

Calculate the normalized cross-correlation map nCCM, which is defined as $$nCCM = \frac{CCM - \min(CCM)}{\max(CCM) - \min(CCM)} \times (\max(PCC) - \min(PCC)) + \min(PCC), \tag{13}$$

where CCM is the cross-correlation map, defined as $$CCM(u, v) = \sum_{x,y} [f(x, y) - \bar{f}][g(x - u, y - v) - \bar{g}], \quad (14)$$

where f and g represent two images, and $\bar{a}$ refers to the two-dimensional mean operator of an image, a. The locations of the maximum and minimum values of CCM indicate the most likely and the most unlikely (respectively) relative shifts of the images. PCC refers to the Pearson correlation coefficient of the two images.

The normalized cross-correlation map nCCM is then fit to a 2D Gaussian function, which is defined as:

$$G(x, y) = A \cdot \exp\left(-\left(\frac{(x - x_0)^2}{2\sigma_x^2} + \frac{(y - y_0)^2}{2\sigma_y^2}\right)\right), \quad (15)$$

where $x_0$ and $y_0$ represent the lateral position of the peak that indicates the shift amount between the two images along the x and y directions, respectively, and A represents the similarity of the two images, f and g.

While embodiments of the present invention have been shown and described, various modifications may be made without departing from the scope of the present invention. For example, in certain embodiments, the functionality of the first and second deep neural networks 10, 12 may be combined into a single deep neural network. The invention, therefore, should not be limited, except to the following claims, and their equivalents.

What is claimed is:

1. A method of using in vivo reflectance confocal microscopy (RCM) images of unstained tissue to generate digitally histological-stained microscopic images of tissue:

providing a first trained, deep neural network that is executed by image processing software, wherein the first trained deep neural network receives as input(s) a plurality of in vivo RCM images of tissue obtained at different depths within the tissue and outputs a plurality of digitally acetic acid-stained images corresponding to the different depths;

providing a second trained, deep neural network that is executed by image processing software, wherein the second trained, deep neural network receives as input (s) the corresponding digitally acetic acid-stained images from the first trained, deep neural network and optionally a plurality of in vivo RCM images and outputs digitally histological-stained images corresponding to the different depths;

obtaining a plurality of in vivo RCM images of the tissue at different depths;

inputting the plurality of in vivo RCM images of the tissue at the different depths to the first trained, deep neural network to obtain digitally acetic acid-stained images of the tissue at the different depths; and inputting the corresponding digitally acetic acid-stained images at the different depths and optionally the plurality of in vivo RCM images to the second trained, deep neural network, wherein the second trained, deep neural network outputs the digitally histological-stained microscopic images at the different depths of the tissue.

2. The method of claim 1, wherein the tissue comprises one of: skin tissue, cervical tissue, mucosal tissue, epithelial tissue.

3. The method of claim 1, wherein the digitally histological-stained images comprises one of the following histology stains: Hematoxylin and Eosin (H&E) stain, hematoxylin, eosin, Jones silver stain, Masson's Trichrome stain, Periodic acid-Schiff (PAS) stains, Congo Red stain, Alcian Blue stain, Blue Iron, Silver nitrate, trichrome stains, Ziehl Neelsen, Grocott's Methenamine Silver (GMS) stains, Gram Stains, acidic stains, basic stains, Silver stains, Nissl, Weigert's stains, Golgi stain, Luxol fast blue stain, Toluidine Blue, Genta, Mallory's Trichrome stain, Gomori Trichrome, van Gieson, Giemsa, Sudan Black, Perls' Prussian, Best's Carmine, Acridine Orange, immunofluorescent stains, immunohistochemical stains, Kinyoun's-cold stain, Albert's staining, Flagellar staining, Endospore staining, Nigrosin, or India Ink stain.

4. The method of claim 1, wherein the first trained, deep neural network is trained with matched acetic acid-stained images or image patches serving as ground truth images and their corresponding reflectance confocal microscopy (RCM) images or image patches of unstained tissue samples serving as network input.

5. The method of claim 1, wherein the second trained, deep neural network is trained with matched chemically/histologically stained images and/or pseudo-stained images serving as ground truth images and acetic acid-stained images or image patches and/or their corresponding reflectance confocal microscopy (RCM) images or image patches of unstained tissue samples, serving as network input.

6. The method of claim 1, wherein the different depths within the tissue comprises between 2 and 20 different depths.

7. The method of claim 1, wherein the second trained, deep neural network or image processing software outputs a mosaic of a plurality of digitally histological-stained microscopic images of the tissue that represent multiple fields of view (FOVs).

8. The method of claim 1, wherein the second trained, deep neural network or image processing software outputs a three-dimensional volumetric image of the tissue that is digitally histological-stained.

9. The method of claim 1, wherein the second trained, deep neural network or image processing software outputs an image of tissue in a vertical plane.

10. The method of claim 5, wherein the matched ground truth images comprise at least some images that include melanocytes.

11. The method of claim 5, wherein the matched acetic acid-stained images or image patches and their corresponding reflectance confocal microscopy (RCM) images or image patches of unstained tissue samples are subject to a series of trained neural networks configured to register pairs of images or image patches for training of the first trained, deep neural network.

12. The method of claim 1, wherein the first and second trained, deep neural networks comprise convolutional neural networks.

13. The method of claim 1, wherein the first and second trained, deep neural networks are trained using a Generative Adversarial Network (GAN) model.

14. The method of claim 1, wherein the second trained, deep neural network outputs digitally histological-stained microscopic images of the tissue in real-time.

15. The method of claim 1, wherein the digitally histological-stained microscopic images and/or the RCM images of the tissue are displayed on a display.

16. A system for generating digitally histological-stained microscopic images from in vivo reflectance confocal microscopy (RCM) images of unstained tissue:

a computing device having image processing software executed thereon or thereby, the image processing software comprising (1) a first trained, deep neural network, wherein the first trained, deep neural network receives as input(s) a plurality of in vivo RCM images of unstained tissue obtained at different depths and outputs a plurality of digitally acetic acid-stained images corresponding to the different depths; and (2) a second trained, deep neural network, wherein the second trained, deep neural network receives as input(s) the corresponding digitally acetic acid-stained images at the different depths from the first trained, deep neural network and optionally a plurality of in vivo RCM images and outputs digitally histological-stained images at the different depths.

17. The system of claim 16, wherein the digitally histological-stained image comprises one of the following histology stains: Hematoxylin and Eosin (H&E) stain, hematoxylin, eosin, Jones silver stain, Masson's Trichrome stain, Periodic acid-Schiff (PAS) stains, Congo Red stain, Alcian Blue stain, Blue Iron, Silver nitrate, trichrome stains, Ziehl Neelsen, Grocott's Methenamine Silver (GMS) stains, Gram Stains, acidic stains, basic stains, Silver stains, Nissl, Weigert's stains, Golgi stain, Luxol fast blue stain, Toluidine Blue, Genta, Mallory's Trichrome stain, Gomori Trichrome, van Gieson, Giemsa, Sudan Black, Perls' Prussian, Best's Carmine, Acridine Orange, immunofluorescent stains, immunohistochemical stains, Kinyoun's-cold stain, Albert's staining, Flagellar staining, Endospore staining, Nigrosin, or India Ink stain.

18. The system of claim 16, wherein the tissue comprises one of: skin tissue, cervical tissue, mucosal tissue, epithelial tissue.

19. The system of claim 16, wherein the first trained, deep neural network is trained with matched acetic acid-stained images or image patches serving as ground truth images and their corresponding reflectance confocal microscopy (RCM) images or image patches of unstained tissue samples, serving as network input.

20. The system of claim 16, wherein the second trained, deep neural network is trained with matched chemically/histologically stained images and/or pseudo-stained images serving as ground truth images and acetic acid-stained images or image patches and/or their corresponding reflectance confocal microscopy (RCM) images or image patches of unstained tissue samples, serving as network input.

21. The system of claim 16, further comprising a reflectance confocal microscope (RCM) configured to obtain the plurality of in vivo RCM images of the unstained tissue obtained at different depths.

22. The system of claim 16, wherein the first and second trained, deep neural networks comprise convolutional neural networks.

23. The system of claim 16, wherein the first and second trained, deep neural networks are trained using a Generative Adversarial Network (GAN) model.

24. The system of claim 16, further comprising a display for displaying the digitally histological-stained microscopic images of unstained tissue.

25. The system of claim 16, wherein the plurality of in vivo RCM images are obtained from a bench-top or portable RCM device.

26. A method of using in vivo images of unstained tissue to generate digitally histological-stained microscopic images of tissue:

providing a first trained, deep neural network that is executed by image processing software, wherein the first trained deep neural network receives as input(s) a plurality of in vivo images of unstained tissue obtained at different depths within the tissue and outputs a plurality of digitally acetic acid-stained images corresponding to the different depths of the tissue;

providing a second trained, deep neural network that is executed by image processing software, wherein the second trained, deep neural network receives as input (s) the corresponding digitally acetic acid-stained images from the first trained, deep neural network and optionally a plurality of in vivo images and outputs digitally histological-stained images corresponding to the different depths;

obtaining a plurality of in vivo images of the tissue at different depths;

inputting the plurality of in vivo images of the tissue to the first trained, deep neural network to obtain digitally acetic acid-stained images of the tissue at the different depths; and inputting the corresponding digitally acetic acid-stained images at the different depths and optionally the plurality of in vivo images to the second trained, deep neural network, wherein the second trained, deep neural network outputs the digitally histological-stained microscopic images at the different depths of the tissue.

27. The method of claim 26, wherein the obtained plurality of in vivo images of the tissue at different depths comprise multiphoton microscopy images, fluorescence confocal microscopy images, fluorescence lifetime microscopy (FLIM) images, fluorescence microscopy images, hyperspectral microscopy images, Raman microscopy images, structured illumination microscopy images, or polarization microscopy images.

* * * * *